(12) United States Patent
Johansen et al.

(10) Patent No.: US 11,076,609 B2
(45) Date of Patent: Aug. 3, 2021

(54) USE OF LACTIC ACID BACTERIA FOR PREPARING FERMENTED FOOD PRODUCTS WITH INCREASED NATURAL SWEETNESS

(71) Applicant: Chr. Hansen A/S, Hoersholm (DK)

(72) Inventors: Eric Johansen, Hoersholm (DK); Kim Ib Soerensen, Farum (DK); Mirjana Curic-Bawden, Brookfield, WI (US); Mette Pia Junge, Hilleroed (DK)

(73) Assignee: CHR. HANSEN A/S, Hoersholm (DK)

( * ) Notice: Subject to any disclaimer, the term of this patent is extended or adjusted under 35 U.S.C. 154(b) by 0 days.

(21) Appl. No.: 16/655,806

(22) Filed: Oct. 17, 2019

(65) Prior Publication Data
US 2020/0093149 A1    Mar. 26, 2020

Related U.S. Application Data

(62) Division of application No. 14/396,249, filed as application No. PCT/EP2013/058655 on Apr. 25, 2013.

(30) Foreign Application Priority Data

Apr. 25, 2012  (EP) ..................... 12165517
Dec. 20, 2012  (EP) ..................... 12198766

(51) Int. Cl.
| | |
|---|---|
| *C12N 15/01* | (2006.01) |
| *C12N 9/12* | (2006.01) |
| *A23C 9/123* | (2006.01) |
| *A23C 19/032* | (2006.01) |
| *C12N 1/20* | (2006.01) |
| *C12N 15/10* | (2006.01) |
| *C12N 15/74* | (2006.01) |

(52) U.S. Cl.
CPC ........ *A23C 9/1238* (2013.01); *A23C 19/0323* (2013.01); *C12N 1/20* (2013.01); *C12N 9/1205* (2013.01); *C12N 15/01* (2013.01); *C12N 15/1034* (2013.01); *C12N 15/746* (2013.01); *A23Y 2220/15* (2013.01); *A23Y 2240/75* (2013.01)

(58) Field of Classification Search
None
See application file for complete search history.

(56) References Cited

U.S. PATENT DOCUMENTS

2015/0086675 A1  3/2015  Johansen et al.

FOREIGN PATENT DOCUMENTS

| CN | 101586087 | 11/2009 |
|---|---|---|
| WO | WO-2005/003327 A1 | 1/2005 |
| WO | WO-2006/039768 | 4/2006 |
| WO | WO-2011/026863 A1 | 3/2011 |

OTHER PUBLICATIONS

Boels et al., "Engineering of Carbon Distribution between Glycolysis and Sugar Nucleotide Biosynthesis in *Lactococcus lactis*", Applied and Environmental Microbiology, vol. 69, No. 2, 2003, pp. 1129-1135.
Chervaux et al., "Physiological Study of *Lactobacillus delbrueckii* subsp. *bulgaricus* Strains in a Novel Chemically Defined Medium", Applied and Environmental Microbiology, vol. 66, No. 12, 2000, pp. 5306-5311.
Cochu et al., "Genetic and Biochemical Characterization of the Phosphoenolpyruvate:Glucose/Mannose Phosphotransferase System of *Streptococcus thermophilus*", Applied and Environmental Microbiology, vol. 69, No. 9, 2003, pp. 5423-5432.
De Vin et al., "Molecular and Biochemical Analysis of the Galactose Phenotype of Dairy *Streptococcus thermophilus* Strains Reveals Four Different Fermentation Profiles", Applied and Environmental Microbiology, vol. 71, No. 7, 2005, pp. 3659-3667.
De Vos et al: "Engineering metabolic highways in Lactococci and other lactic acid bacteria", Trends in Biotechnology, vol. 22, No. 2, 2004, pp. 72-79.
Delorme et al., "Emergence of a Cell Wall Protease in the *Streptococcus thermophilus* Population", Applied and Environmental Microbiology, vol. 76, No. 2, 2010, pp. 451-460.
Gauthier et al: "Positive selection for resistance to 2-deoxyglucose gives rise, in *Streptococcus salivarius*, to seven classes of pleiotropic mutants, including ptsH and ptsI missense mutants" Molecular Microbiology, vol. 13, No. 6, pp. 1101-1109 (1994).
Godshall, "The Role of Carbohydrates in Flavor Development", Food Technology, 1988, pp. 71-78.
Høier et al., "The Production, Application and Action of Lactic Cheese Starter Cultures" In: The Technology of Cheesemaking, Chapter 5, 2nd Ed. Blackwell Publishing, Oxford, 2010, p. 166-192.
Hols et al., "New Insights in the molecular biology and physiology of *Streptococcus thermophilus* revealed by comparative genomics", FEMS Microbiology Reviews, vol. 29, 2005, pp. 435-463.

(Continued)

*Primary Examiner* — Rebecca E Prouty
(74) *Attorney, Agent, or Firm* — Foley & Lardner LLP

(57) ABSTRACT

Described are mutant *Streptococcus thermophilus* strains and mutant *Lactobacillus delbrueckii* subsp. *bulgaricus* strains that excrete glucose into milk when the milk is inoculated and fermented with such strains. Methods for obtaining such strains without genetic modification are described, including methods for obtaining such *Streptococcus thermophilus* strains by selecting and isolating from a pool of *Streptococcus thermophilus* strains derived from a galactose-fermenting *Streptococcus thermophilus* mother strain a pool of *Streptococcus thermophilus* strains which are resistant to 2-deoxyglucose, and selecting and isolating from the pool of *Streptococcus thermophilus* strains which are resistant to 2-deoxyglucose a *Streptococcus thermophilus* strain which exhibits a growth rate in M17 medium+2% galactose higher than its growth rate in M17 medium+2% glucose. The strains are useful for decreasing the lactose content of a fermented food product and for boosting growth of the probiotic BB-12®.

5 Claims, 4 Drawing Sheets

Specification includes a Sequence Listing.

(56) References Cited

OTHER PUBLICATIONS

Hopkins et al., "Inter-species differences in maximum specific growth rates and cell yields of bifidobacteria cultured on oligosaccharides and other simple carbohydrate sources", Journal Applied Microbiology, vol. 85, 1998, pp. 381-386.
Hutkins et al., "Use of Galactose-Fermenting *Streptococcus thermophilus* in the Manufacture of Swiss, Mozzarella, and Short-Method Cheddar Cheese", J. Dairy Sci., vol. 69, No. 1, 1986, pp. 1-8.
International Search Report dated Jun. 6, 2013 issued in PCT/EP2013/058655.
Karlin et al., "Applications and statistics for multiple high-scoring segments in molecular sequences", Proc. Natl. Acad. Sci. USA, vol. 90, 1993, pp. 5873-5877.
Karlin et al., "Methods for assessing the statistical significance of molecular sequence features by using general scoring schemes", Proc. Natl. Acad. Sci. USA, vol. 87, 1990, p. 2264-2268.
Myers et al., "Optimal alignments in linear space", Comput. Appl. Biosci., vol. 4, 1988, pp. 11-17.
Makarova et al., "Comparative genomics of the lactic acid bacteria," PNAS 103(42): 15611-15616 (2006).
Needleman et al., "A General Method Applicable to the Search for Similarities in the Amino Acid Sequence of Two Proteins", J. Mol. Biol., vol. 48, 1970, pp. 443-453.
Pearson et al., "Improved tools for biological sequence comparison", Proc. Natl. Acad. Sci. USA, vol. 85, 1988, pp. 2444-2448.
Pool et al: "Natural sweetening of food products by engineering *Lactococcus lactis* for glucose production", Metabolic Engineering, vol. 8, 2006, pp. 456-464.
Porter et al., "Purification and Kinetic Characterization of a specific Glucokinase from *Streptococcus mutans* OMZ70 Cells", Biochim. Biophys. Acta., vol. 709, 1982, pp. 178-186.
Thompson et al: "Lactose Metabolism in *Streptococcus lactis*: Studies with a Mutant Lacking Glucokinase and Mannose-Phosphotransferase Activities", Journal of Bacteriology, vol. 162, No. 1, 1985, pp. 217-223.
Vadeboncoeur et al., "Control of sugar utilization in the oral bacteria *Streptococcus salivarius* and *Streptococcus sanguis* by the phosphoenolpyruvate: Glucose phosphotransferase system", Archives of Oral Biology, Pergamon Press, Oxford, GB, vol. 28, No. 2, 1983, pp. 123-131.
Vaillancourt et al., "Galactose and Lactose Genes from the Galactose-Positive Bacterium *Streptococcus salivarius* and the Phylogenetically Related Galactose-Negative Bacterium *Streptococcus thermophilus*: Organization, Sequence, Transcription, and Activity of the gal Gene Products", J. Bacteriol., vol. 184, No. 3, 2002, pp. 785-793.
Vaughan et al., "Activation of Silent gal Genes in the lac-gal Regulon of *Streptococcus thermophiles*," J. Bacteriol., 183(4): 1184-1194 (2001).
Ibrahim et al., "Use of Chemical Mutagenesis for the Isolation of Food Grade β-Galactosidase Overproducing Mutants of Bifidobacteria, Lactobacilli and *Streptococcus thermophilus*," J Dairy Sci (2000) 83:923-930.

```
      MetSerLysLys LeuLeuGly IleAspLeu GlyGlyThrThr ValLysPhe GlyIleLeu ThrAlaAspGly GluValGln GluLysTrp AlaIleGluThr·
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
   1  ATGAGTAAGA AACTCTTAGG TATTGACCTT GGTGGAACAA CTGTTAAGTT TGGTATTTTG ACTGCAGATG GTGAAGTTCA AGAAAAATGG GCTATTGAAA

·TAsnThrPhe GluAsnGly SerHisIleVal ProAspIle ValGluSer LeuLysHisArg LeuGluLeu TyrGlyLeu ThrAlaGluAsp PheIleGly·
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 101  CAAATACGTT TGAAAATGGT AGCCACATTG TTCCTGACAT TGTAGAATCT TTGAAACACC GTTTGGAATT GTATGGACTT ACTGCTGAAG ATTTTATTGG
                    Pro
      ·IleGlyMet GlySerProGly AlaValAsp ArgGluAsn LysThrValThr GlyAlaPhe AsnLeuAsn TrpAlaGluThr GlnGluVal GlySerVal
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 201  AATTGGTATG GGATCTCCAG GTGCAGTTGA CCGAGAAAAT AAAACAGTAA CGGGTGCCTT TAACTTGAAC TGGGCAGAAA CTCAAGAAGT TGGCTCTGTT
CHCC15887          C
      IleGluLysGlu LeuGlyIle ProPheAla IleAspAsnAsp AlaAsnVal AlaAlaLeu GlyGluArgTrp ValGlyAla GlyAlaAsn AsnArgAsnVal·
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 301  ATTGAAAAAG AACTTGGTAT TCCATTCGCT ATTGATAATG ATGCTAATGT GGCTGCACTG GGTGAACGTT GGGTTGGTGC TGGTGCTAAC AATCGGAATG
                          Ile
      ·VValPheIle ThrLeuGly ThrGlyValGly GlyGlyVal IleAlaAsp GlyAsnLeuIle HisGlyVal AlaGlyAla GlyGlyGluIle GlyHisIle·
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 401  TTGTCTTTAT AACATTGGGT ACAGGTGTTG GTGGCGGTGT TATCGCTGAT GGTAACTTAA TTCATGGTGT TGCCGGTGCT GGTGGGGAAA TTGGTCACAT
CHCC15757                   T
      ·IleValGlu ProAspThrGly PheGluCys ThrCysGly AsnLysGlyCys LeuGluThr ValAlaSer AlaThrGlyIle ValArgVal AlaHisHis
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 501  TATTGTTGAA CCTGACACAG GATTTGAGTG TACTTGCGGA AACAAGGGGT GTCTGGAAAC TGTAGCTTCA GCAACAGGTA TTGTACGTGT AGCACATCAT

LeuAlaGluLys TyrGluGly AsnSerSer IleLysAlaAla ValAspAsn GlyGluPhe ValThrSerLys AspIleIle ValAlaAla ThrGluGlyAsp·
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 601  TTGGCAGAAA AATACGAAGG AAACTCTTCT ATTAAAGCTG CTGTAGACAA TGGTGAGTTT GTGACAAGTA AAGATATTAT CGTAGCTGCT ACTGAAGGTG

·ALysPheAla AspSerIle ValAspLysVal SerLysTyr LeuGlyLeu AlaThrAlaAsn IleSerAsn IleLeuAsn ProAspSerVal ValIleGly·
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 701  ATAAGTTTGC TGACAGCATT GTTGATAAAG TCTCTAAATA CCTCGGACTT GCAACAGCAA ACATCTCAAA CATTCTTAAC CCAGATTCTG TCGTTATCGG

·GlyGlyVal SerAlaAlaGly GluPheLeu ArgSerArg ValGluGlyTyr PheThrArg TyrAlaPhe ProGlnValArg ArgThrThr LysValLys
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 801  TGGTGGTGTT TCTGCCGCAG GAGAATTCTT GCGTAGTCGT GTTGAAGGAT ACTTTACACG TTATGCATTC CCACAAGTTC GCCGTACAAC AAAAGTGAAA

LeuAlaGluLeu GlyAsnAsp AlaGlyIle IleGlyAlaAla SerLeuAla TyrSerIle AspLys*            (SEQ ID NO. 2)
      ~~~~~~~~~~~~~~~~~~~~~~~~~~~~~~~~~~~~~~~~~~~~~~~~~~~~~~~~~~~~~~~~~~~
 901  TTAGCGGAGC TTGGAAATGA TGCAGGAATC ATTGGAGCTG CTAGTCTTGC TTATAGTATT GACAAATAA   (SEQ ID NO. 1)
```

Figure 2

```
            M   S   D   M   S   I   I   S   A   I   L   V   V   A   V   F   L   A   G
  1   ATGTCAGATA TGTCAATTAT TTCTGCGATT TTGGTCGTAG CTGTTGCCTT CCTTGCTGGT
        L   E   S   I   L   D   Q   F   Q   F   H   Q   P   L   V   A   C   T   L   I
 61   CTTGAAAGTA TCCTTGACCA ATTCCAATTC CACCAACCAC TTGTTGCATG TACCCTCATC
          G   A   A   T   G   N   L   T   A   G   I   M   L   G   G   S   L   Q   M   I
121   GGTGCTGCCA CAGGTAACCT CACTGCAGGT ATCATGCTTG GTGGTTCTCT TCAAATGATT
        T   L   A   W   A   N   I   G   A   A   V   A   P   D   V   A   L   A   S   V
181   ACCCTTGCTT GGGCAAACAT CGGTGCTGCC GTAGCTCCTG ACGTTGCCCT TGCATCTGTT
        A   A   A   I   I   L   V   K   G   G   K   F   T   A   E   G   I   G   V   A
241   GCCGCTGCCA TCATTTTGGT TAAAGGTGGT AAATTTACAG CTGAAGGTAT CGGTGTTGCG
        I   A   I   A   I   L   L   A   V   A   G   L   F   L   T   M   P   V   R   T
301   ATTGCAATAG CTATCCTGCT TGCAGTTGCA GGTCTCTTCC TAACTATGCC TGTTCGTACA
        A   S   I   A   F   V   H   A   A   D   K   A   A   E   H   G   N   I   A   G
361   GCATCTATTG CCTTTGTTCA TGCTGCAGAT AAAGCTGCAG AACACGGAAA CATCGCTGGT
            V   E   R   A   Y   Y   L   A   L   L   L   Q   G   L   R   I   A   V   P   A
421   GTTGAACGTG CATACTACCT CGCTCTCCTT CTTCAAGGTT TGCGTATTGC TGTGCCAGCA
        A   L   L   L   A   I   P   A   Q   S   V   Q   H   A   L   G   L   M   P   D
481   GCCCTTCTTC TTGCCATCCC GGCCCAATCT GTTCAACATG CCCTTGGCTT GATGCCTGAC
          W   L   T   H   G   L   V   V   G   G   G   M   V   V   A   V   G   Y   A   M
541   TGGCTCACCC ATGGTTTGGT TGTCGGTGGT GGTATGGTCG TAGCCGTTGG TTACGCCATG
          I   I   N   M   M   A   T   R   E   V   W   P   F   F   A   I   G   F   A   L
601   ATTATCAATA TGATGGCTAC TCGTGAAGTT TGGCCATTCT TCGCCATTGG TTTTGCTTTG
CHCC16404                       T
          A   A   I   S   Q   L   T   L   I   A   L   S   T   I   G   V   A   I   A   F
661   GCAGCAATTA GCCAATTGAC ACTTATCGCT CTTAGTACCA TTGGTGTTGC CATCGCCTTC
          I   Y   L   N   L   S   K   Q   G   G   G   N   G   G   G   N   G   G   G   T
721   ATCTACCTCA ACCTTTCTAA ACAAGGTGGC GGAAATGGTG GCGGAAATGG TGGCGGAACT
          S   S   G   S   G   D   P   I   G   D   I   L   E   D   Y       (SEQ ID NO.6)
781   TCATCTGGTT CAGGCGACCC AATCGGCGAT ATCTTGGAAG ACTAC        (SEQ ID NO.5)
```

Figure 4

USE OF LACTIC ACID BACTERIA FOR PREPARING FERMENTED FOOD PRODUCTS WITH INCREASED NATURAL SWEETNESS

CROSS-REFERENCE TO RELATED APPLICATIONS

The present application is a divisional of U.S. application Ser. No. 14/396,249, filed Oct. 22, 2014, which is the U.S. National Stage of International Application No. PCT/EP2013/058655, filed Apr. 25, 2013, and claims priority to European Patent Application Nos. 12165517.9, filed Apr. 25, 2012, and 12198766.3, filed Dec. 20, 2012.

SEQUENCE LISTING

The instant application contains a Sequence Listing which has been submitted electronically in ASCII format and is hereby incorporated by reference in its entirety. Said ASCII copy, created on Oct. 22, 2014, is named Sequence_Listing.txt and is 8,457 bytes in size.

FIELD OF INVENTION

The present invention relates to *Streptococcus thermophilus* bacteria strains and cultures with a sweetening property by excretion of high levels of glucose formed by degradation of lactose, *Lactobacillus delbrueckii* subsp. *bulgaricus* bacteria strains with a sweetening property by excretion of high levels of glucose formed by degradation of lactose, starter cultures comprising such strains, and dairy products fermented with the cultures. The present invention also relates to a method of obtaining such strains and the use of such strains for the preparation of fermented milk products and for increasing the sweetness of fermented milk products while decreasing the lactose content of the fermented milk products.

BACKGROUND OF THE INVENTION

Pure fermented milk products are recognized by a tart or sour taste as a result of the conversion of lactose to lactic acid by lactic acid bacteria during fermentation. They are, therefore, often sweetened by the addition of fruit, honey, sugar or artificial sweeteners to accommodate the customers' desire for a sweeter tasting product.

The food industry has an increasingly high demand for low-calorie sweet-tasting food products in order to help overcome the overweight and obesity problems that have become so prevalent in the last 20 years. Sweetness, usually regarded as a pleasurable sensation, is produced by the presence of sugars and a few other substances. The perception of sugars is very different. Using sucrose as a 100 reference, the sweetness of lactose is 16, of galactose 32 and of glucose 74 (Godshall (1988). Food Technology 42(11): 71-78). Glucose is thus perceived more than 4 times sweeter than lactose while still having approximately the same level of calories.

Sugar in fermented food products is more often being replaced with sweeteners such as aspartame, acesulfame K, sucralose and saccharin which can provide the sweetness with a lower intake of calories. However, the use of artificial sweeteners may result in an off-taste and several studies indicating that the consumption of artificial sweeteners are connected with drawbacks, such as increasing hunger, allergies, cancer etc., have contributed to consumer's preference for fermented milk products which only contain natural sweeteners or, preferably, contain no added sweetener.

Thus, a special challenge lies in developing fermented milk products where the natural (inner) sweetness is high.

The acidity of fermented milk products depend in large part on the lactic acid bacteria present and the process parameters used for preparing the fermented milk product.

Fermentation of the disaccharide lactose is very much studied in lactic acid bacteria because it is the major carbon source in milk. In many species, lactose is cleaved by β-galactosidase into glucose and galactose after uptake. The glucose is phosphorylated by glucokinase to glucose-6-phosphate and fermented via the Embden-Meyerhof-Parnas pathway (glycolysis) by most lactic acid bacteria (FIG. 1).

*Streptococcus thermophilus* is one of the most widely used lactic acid bacteria for commercial thermophilic milk fermentation where the organism is normally used as part of a mixed starter culture, the other component being a *Lactobacillus* sp., e.g. *Lactobacillus delbrueckii* subsp. *bulgaricus* for yoghurt or *Lactobacillus helveticus* for Swiss-type cheese.

The legal definition of yoghurt in many countries requires *Streptococcus thermophilus* alongside *Lactobacillus delbrueckii* subsp. *bulgaricus*. Both species generate desirable amounts of acetaldehyde, an important flavor component in yoghurt.

Lactose and sucrose are fermented more readily by *Streptococcus thermophilus* than their component monosaccharides. In the presence of excess galactose only the glucose portion of the lactose molecule is fermented and galactose accumulates in fermented milk products when *Streptococcus thermophilus* is used. In yoghurt wherein high acid concentrations limit the fermentation, free galactose remains while the free galactose produced in the early stages of Swiss cheese manufacture is later fermented by *Lactobacillus helveticus*.

However, galactose fermenting strains of both *Streptococcus thermophilus* and *Lactobacillus delbrueckii* subsp. *bulgaricus* have been reported by several researchers (Hutkins et al. (1986) J. Dairy Sci. 69(1): 1-8; Vaillancourt et al. (2002) J. Bacteriol. 184(3); 785-793) and in WO 2011/026863 (Chr. Hansen) is described a method for obtaining *Streptococcus thermophilus* strains which are galactose fermenting.

In order to meet the requirements of the food industry, it has become relevant to propose new strains, in particular *Streptococcus thermophilus* strains and *Lactobacillus delbrueckii* subsp. *bulgaricus* strains, which provide more natural sweetness without extra calories directly into the fermented product (inner sweetness) by excretion of glucose.

Pool et al. (2006. Metabolic Engineering 8(5); 456-464) discloses *Lactococcus lactis* strain in which the glucose metabolism is completely disrupted by deletion of the genes coding for glucokinase, EII(man/glc) and the newly discovered glucose-PTS EII(cel). The construction method is genetic recombination for generation of all the mutations and the resulting strain is consequently a genetically modified organism (GMO) that at present can not be used in food products.

Thompson et al. (1985. J Bacteriol. 162(1); 217-223) studied the lactose metabolism in *Streptococcus lactis* (today renamed *Lactococcus lactis*). In this work 2-deoxyglucose was used to obtain a mutant in the mannose-PTS system. Subsequently, this mutant was mutagenized using UV mutagenesis followed by screening for glucose-negative colonies by replica plating. In this way a double mutant (mannose PTS and glucokinase) was isolated. This double mutant was used to study the mechanisms involved in the regulation of lactose fermentation by "starter" organisms. These mutants have several disadvantages compared to their parent strain which makes them unsuitable for inclusion in a commercial starter culture. The cell yield of the mutants was half that of the parent strain per mole of lactose fermented and the doubling time was significantly increased in the mutants when grown on lactose. Likewise, the yield of lactic acid was half that of the parent strain per mole of lactose fermented. The behavior of these strains in milk was not analyzed but it Is anticipated that the rate of acidification would be significantly reduced.

In addition, Lactococcus lactis is generally not chosen for acetaldehyde production and does not contribute to the fulfillment of the requirements for the legal definition of yoghurt.

Chervaux et al. (2000. Appl. And Environ. Microbiol., 66, 5306-5311), studied the physiology of Lactobacillus delbrueckii subsp. bulgaricus strains in a novel chemically defined medium and isolated 2-deoxyglucose-resistant mutants that were deficient in glucose fermentation. Several different phenotypes were observed and strain-specific effects were reported.

None of the above approaches solve the problem of providing Streptococcus thermophilus strains and Lactobacillus delbrueckii subsp. bulgaricus strains with enhanced properties for natural sweetening of food products that are fermented using such strains alone or together with other lactic acid bacteria strains.

Additionally, none of the above approaches solve the problem of decreasing the lactose content in food products that are fermented using such strains to a level tolerable to lactose intolerant individuals.

SUMMARY OF INVENTION

In contrast to the prior art described above, the present inventors have found that Streptococcus thermophilus strains with a mutation in the glucokinase (glcK) gene can be selected by exposure of galactose-fermenting Streptococcus thermophilus strains to 2-deoxygluxose and that these cells digest lactose and galactose and excrete glucose to the environment when grown on a milk substrate.

Surprisingly, these Streptococcus thermophilus strains alone are still fully capable of acidifying milk although acidification time to pH 5 is delayed by 2-5 hours. They are therefore as such useful in fermented milk applications.

However, glucose is used as a carbon source by many lactic acid bacteria and any excreted glucose can be consumed by other microorganisms present in the fermented milk product.

To overcome this problem, the present invention provides 2-deoxyglucose-resistant mutants of Lactobacillus delbrueckii subsp. bulgaricus which have either lost the ability to grow on glucose as carbon source or exhibit an impaired ability to grow under such conditions. The mutant strains of Lactobacillus delbrueckii subsp. bulgaricus not only do not consume glucose secreted into the milk by other microorganisms that might be present, they also excrete high amounts of glucose into the surrounding medium and are, surprisingly, still fully capable of acidifying milk although acidification time to pH 5 is delayed by 2-5 hours. They are therefore as such useful in fermented milk applications.

Such food grade bacteria can be used to fortify fermented milk products with glucose. Glucose has a higher perceived sweetness than both lactose and galactose and as such the excretion of glucose to the milk substrate will result in a higher perceived (inner) sweetness in the fermented milk product.

The inventors of the present invention found that when a milk substrate is fermented with a Streptococcus thermophilus strain and a Lactobacillus delbrueckii subsp. bulgaricus strain according to the invention the lactose level within the milk decreases significantly.

Lactose intolerance is a condition caused by the inability to digest lactose. Most lactose-intolerant individuals can tolerate some amount of lactose in their diet and the severity of their symptoms (including nausea, cramping, bloating, diarrhea, and flatulence) increases with the amount of lactose consumed.

Thus, it is of great importance in the industry to be able to produce food products which are either lactose-free or which have a reduced lactose content.

No common limit values have so far been defined in EU for the lactose content of low-lactose and lactose-free food products but the Finnish Food Safety Authority Evira states that Nordic limit values are a lactose content of less than 10 mg/100 g or 100 ml for lactose-free foods and a lactose content of less than 1 g/100 g or 100 ml for low-lactose foods.

The dairy industry today faces a problem of providing an alternative to adding sweeteners to fermented milk products in order to achieve the desired sweet taste without the added calories. Furthermore, it would be highly advantageous to establish a method for reducing lactose in fermented milk products to a level which will be acceptable for lactose-intolerant consumers.

The above problems have been solved by providing mutant Streptococcus thermophilus strains and mutant Lactobacillus delbrueckii subsp. bulgaricus strains that excrete glucose into the milk when 9.5% B-milk is inoculated with $10^6$-$10^7$ CFU/ml of a Streptococcus thermophilus strain according to the invention or with $10^6$-$10^7$ CFU/ml of a Lactobacillus delbrueckii subsp. bulgaricus strain according to the invention and fermented with the Streptococcus thermophilus strains or the Lactobacillus delbrueckii subsp. bulgaricus strain according to the invention at 40° C. for at least 20 hours. Preferably, such mutant strains alone will excrete at least 5 mg/ml glucose into B-milk when 9.5% B-milk is inoculated with $10^6$-$10^7$ CFU/ml of a Streptococcus thermophilus strain according to the invention or with $10^6$-$10^7$ CFU/ml of a Lactobacillus delbrueckii subsp. bulgaricus strain according to the invention and fermented with the Streptococcus thermophilus strains or the Lactobacillus delbrueckii subsp. bulgaricus strain according to the invention at 40° C. for at least 20 hours. The strains are still fully capable of acidifying milk although acidification time to pH 5 is delayed by 2-5 hours. The final fermented milk contains less than 15 mg/ml lactose in the fermented milk. The final fermented milk consequently has a higher inner sweetness index of approximately 2 fold or more.

To provide the Streptococcus thermophilus strains, the present inventors have found a method of isolating 2-deoxyglucose resistant mutant strains from a galactose-fermenting Streptococcus thermophilus mother strain, preferably one with a mutation in the galactose operon which increases the expression of a previously lowly expressed or not expressed operon, wherein the 2-deoxyglucose resistance phenotype is caused by a mutation in the glucokinase (glcK) gene that partially or totally inactivates the encoded protein. The method comprises subjecting the mother strain to 2-deoxyglucose and selecting mutant strains that are able to grow in the presence of 2-deoxyglucose on agar plates containing M17 medium+2% galactose, such as described in Example 1 herein. These mutants are screened and strains that have a growth rate which is higher in M17 medium+2% galactose than in M17 medium+2% glucose are chosen.

It was surprisingly found that the mutant strains of *Streptococcus thermophilus* with a mutation in the glucokinase gene (glcK) but with an apparently normally functioning glucose transporter system were secreting glucose. These mutants were named, CHCC15757 and CHCC15887.

Furthermore, the inventors found that strains of *Streptococcus thermophilus* with an even higher capability for fermentation of lactose and excretion of glucose could be selected by subjecting the strains of *Streptococcus thermophilus* with a mutation in the glucokinase gene to 2-deoxyglucose and selecting strains which are unable to grow in 9.5% B-milk except when sucrose is added to the B-milk in a concentration of as little as 0.01%. One such hyper-lactose fermenting and glucose secreting mutant was named CHCC16404.

It was found that CHCC16404 has a mutation in a glucose transporter gene (manM) resulting in the inactivation of a glucose transporter protein responsible for transport of glucose into the cell.

To provide the *Lactobacillus delbrueckii* subsp. *bulgaricus* strains, the present inventors have found a method of isolating 2-deoxyglucose resistant mutant strains of a *Lactobacillus delbrueckii* subsp. *bulgaricus* mother strain, which has either lost the ability to grow on glucose as carbon source or has an impaired ability to grow on glucose as carbon source. The method comprises subjecting the mother strain to 2-deoxyglucose and selecting mutant strains that are able to grow in the presence of 2-deoxyglucose on agar plates containing MRS-IM medium containing 2% lactose, such as described in Example 5 herein. These mutants are screened and strains that have either completely lost or have an Impaired ability to grow on MRS-IM containing 2% glucose when compared with the mother strain that can grow glucose are chosen.

In accordance with this surprising finding, the present invention relates to novel strains of lactic acid bacteria, such as in particular *Streptococcus thermophilus* with a mutation in the glcK gene or *Lactobacillus delbrueckii* subsp. *bulgaricus* mutants, that excrete glucose into the fermented product to provide a natural sweetness without extra calories, a method for producing the strains, fermented milk products made using such strains and use of such strains for preparing fermented milk products with increased sweetness and decreased levels of lactose.

Furthermore, the *Streptococcus thermophilus* and *Lactobacillus delbrueckii* subsp. *bulgaricus* strains of the invention were, surprisingly, found to boost the growth of *Bifidobacterium animalis* subsp. *lactis* strain BB-12®, a probiotic bacterium which does not grow well when present alone in milk.

BRIEF DESCRIPTION OF THE DRAWINGS

FIG. 2 depicts the DNA sequence (SEQ ID NO. 1) of the glucokinase gene (glcK) of *Streptococcus thermophilus* as well as the encoded amino acid sequence (SEQ ID NO. 2). The single nucleotide substitutions found in CHCC15757 and CHCC15887, respectively, are indicated.

FIG. 4 depicts the DNA sequence (SEQ ID NO. 5) of the manM gene of *Streptococcus thermophilus* strain CHCC15757 as well as the encoded amino acid sequence (SEQ ID NO. 6). The single nucleotide substitution found in CHCC16404 is indicated.

DETAILED DISCLOSURE OF THE INVENTION

Figure 1:
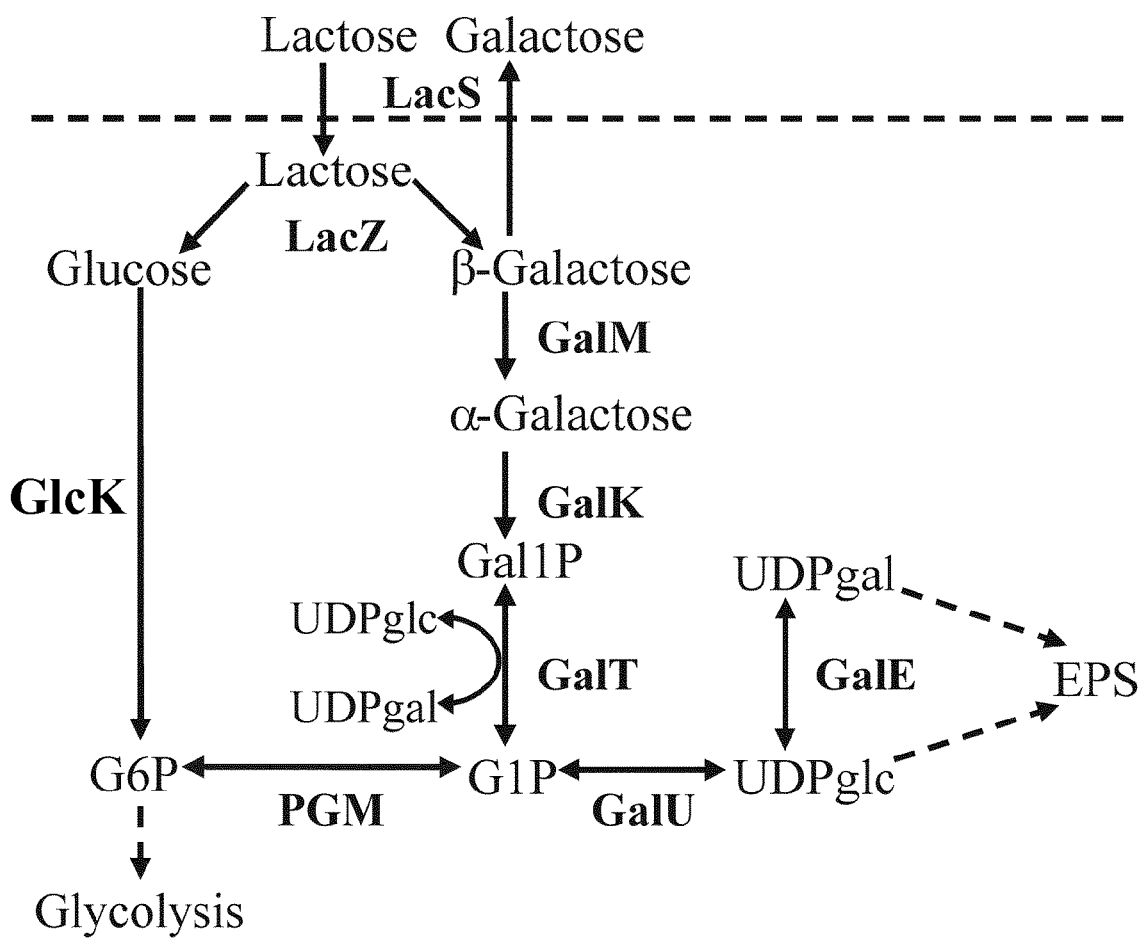
FIG. 1 is a schematic representation of lactose catabolism in *Streptococcus thermophilus*. GlcK, glucokinase; LacS, lactose transporter; LacZ, β-galactosidase; GalM, mutarotase; GalK, galactokinase; GalT, galactose-1-phosphate uridyltransferase; GalE, UDP-glucose 4 epimerase; Gal1P, galactose-1-phosphate.

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "lactobacillales" which includes *Lactococcus* spp., *Streptococcus* spp., *Lactobacillus* spp., *Leuconostoc* spp., *Pediococcus* spp., *Brevibacterium* spp., *Enterococcus* spp. and *Propionibacterium* spp. Lactic acid bacteria, including bacteria of the species *Lactobacillus* sp. and *Streptococcus thermophilus*, are normally supplied to the dairy industry either as frozen or freeze-dried cultures for bulk starter propagation or as so-called "Direct Vat Set" (DVS) cultures, Intended for direct inoculation into a fermentation vessel or vat for the production of a dairy product, such as a fermented milk product. Such cultures are in general referred to as "starter cultures" or "starters".

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring Individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

In some countries, the legal definition of yoghurt requires the presence of both *Streptococcus thermophilus* and *Lactobacillus delbrueckii* subsp. *bulgaricus*. Both species generate desirable amounts of acetaldehyde, an important flavor component in yoghurt.

Cheese, such as Mozzarella and Pizza cheese as well as Feta, can also be prepared by fermentation using both Streptococcus thermophilus and Lactobacillus delbrueckii sub sp. bulgaricus (Høier et al. (2010) in The Technology of Cheesemaking, 2$^{nd}$ Ed. Blackwell Publishing, Oxford; 166-192).

In order to meet the requirements of the food industry, it has become desirable to develop new strains, in particular Lactobacillus delbruckii subsp. bulgaricus strains and Streptococcus thermophilus strains, which produce more natural sweetness directly in the fermented product (inner sweetness) without contributing extra calories.

Streptococcus thermophilus is one of the most widely used lactic acid bacteria for commercial milk fermentation where the organism is normally used as part of a mixed starter culture, the other component being a Lactobacillus sp., e.g. Lactobacillus delbrueckii subsp. bulgaricus for yoghurt and Lactobacillus helveticus for Swiss-type cheese.

Lactose and sucrose are fermented more readily by Streptococcus thermophilus than their component monosaccharides. Only the glucose portion of the lactose molecule is fermented by Streptococcus thermophilus and galactose accumulates in fermented milk products when Streptococcus thermophilus is used. In yoghurt, wherein high acid concentrations limit the fermentation, free galactose remains while the free galactose produced in the early stages of Swiss cheese manufacture is later fermented by Lactobacillus helveticus. Lactococcus lactis found in many starter cultures used for cheese manufacture is also capable of consuming the galactose produced by Streptococcus thermophilus.

In order to ensure Streptococcus thermophilus strains with a growth performance as optimal as possible, the present inventors have exposed galactose-fermenting strains of Streptococcus thermophilus to the selective agent 2-deoxyglucose. Typically 2-deoxyglucose resistant mutants have mutations in the gene encoding glucokinase and in genes coding for glucose transport. The isolated mutants, CHCC15757, CHCC15887 and CHCC16404, which are resistant to 2-deoxyglucose have mutations in their glucokinase (glcK) gene. In addition to a mutation in the glucokinase gene, the present inventors found that CHCC16404 has a stop codon mutation in a glucose/mannose transporter gene which could explain why exported glucose is not transported back into the cells again.

Surprisingly, such mutants alone are still fully capable of acidifying milk although acidification time to pH 5 is delayed by 2-5 hours. They are therefore as such useful in fermented milk applications and they have preserved the ability of the mother strains to clot the milk which is characteristic of yoghurt. Additionally, it was found that the mutants excreted more than 5 mg/ml glucose, when 9.5% B-milk was inoculated with $10^6$-$10^7$ CFU/ml of Streptococcus thermophilus strain CHCC15757 or CHCC15887 and fermented at 40° C. for at least 20 hours without the need for isolation of glucose transport mutants, or when 9.5% B-milk with 0.05% sucrose was inoculated with $10^6$-$10^7$ CFU/ml of Streptococcus thermophilus strain CHCC16404 and fermented at 40° C. for at least 20 hours. At the same time, as little as approximately 10 mg/ml lactose and less than 1.5 mg/ml lactose (detection limit), respectively, remain in the fermented milk. Therefore, the use of such strains for producing fermented milk products may have an importance for people with lactose intolerance.

Consequently, the final fermented milk has a higher inner sweetness index of at least 2.0 calculated as described by Godshall (1988. Food Technology 42(11):71-78).

The first aspect of the present invention, thus, relates to a galactose-fermenting mutant strain of Streptococcus thermophilus, wherein the mutant strain carries a mutation in the DNA sequence of the glcK gene encoding a glucokinase protein, wherein the mutation inactivates the encoded glucokinase protein or has a negative effect on expression of the gene. Methods for measuring the level of glucokinase activity or the level of expression of the glucokinase gene are readily known (Porter et al. (1982) Biochim. Biophys. Acta, 709; 178-186) and include enzyme assays with commercially available kits and transcriptomics or quantitative PCR using materials which are readily available.

A bacterial "strain" as used herein refers to a bacterium which remains genetically unchanged when grown or multiplied. A multiplicity of identical bacteria are included.

The term "galactose-fermenting Streptococcus thermophilus strains" as used herein refers to Streptococcus thermophilus strains which are capable of growth on/in M17 medium+2% galactose. The galactose-fermenting Streptococcus thermophilus strains are defined herein as Streptococcus thermophilus strains which lower the pH of M17 broth containing 2% galactose as sole carbohydrate to 5.5 or lower when inoculated from an overnight culture at 1% and incubated for 24 hours at 37° C.

Galactose-fermenting strains may be obtained by the method described in WO 2011/026863.

The term "the mutation inactivates the glucokinase protein" as used herein refers to a mutation which results in an "inactivated glucokinase protein", a glucokinase protein which, if present in a cell, is not able to exert its normal function as well as mutations which prevent the formation of the glucokinase protein or result in degradation of the glucokinase protein.

In particular, an inactivated glucokinase protein is a protein which compared to a functional glucokinase protein is not able to facilitate phosphorylation of glucose to glucose-6-phosphate or facilitates phosphorylation of glucose to glucose-6-phosphate at a significantly reduced rate. The gene encoding such an inactivated glucokinase protein compared to the gene encoding a functional glucokinase protein comprises a mutation in the open reading frame (ORF) of the gene, wherein said mutation may include, but is not limited to, a deletion, a frameshift mutation, introduction of a stop codon or a mutation which results in an amino acid substitution, which changes the functional properties of the protein, or a promoter mutation that reduces or abolishes transcription or translation of the gene.

In preferred embodiments the mutation reduces the activity (the rate of phosphorylation of glucose to glucose-6-phosphate) of the glucokinase protein with at least 50%, such as at least 60%, such as at least 70%, such as at least 80%, such as at least 90%.

The glucokinase activity can be determined by the glucokinase enzymatic assays as described by Pool et al. (2006. Metabolic Engineering 8; 456-464).

The term "functional glucokinase protein" as used herein refers to a glucokinase protein which, if present in a cell, facilitates phosphorylation of glucose to glucose-6-phosphate. In particular, a functional glucokinase protein may be encoded by a gene comprising an ORF which has a sequence corresponding to position 1-966 in SEQ ID NO. 1 or a sequence which has at least 85% identity, such as at least 90% identity, such as at least 95% identity, such as at least 98% identity, such as at least 99% identity, to the sequence corresponding to position 1-966 of SEQ ID NO. 1.

The percent identity of two sequences can be determined by using mathematical algorithms, such as the algorithm of Karlin and Altschul (1990. Proc. Natl. Acad. Sci. USA 87; 2264), the modified algorithm described in Karlin and Altschul (1993. Proc. Natl. Acad. Sci. USA 90; 5873-5877); the algorithm of Myers and Miller (1988. CABIOS 4; 11-17); the algorithm of Needleman and Wunsch (1970. J. Mol. Biol. 48; 443-453); and algorithm of Pearson and Lipman (1988. Proc. Natl. Acad. Sci. USA 85; 2444-2448). Computer software for the determination of nucleic acid or amino acid sequence identity based on these mathematical algorithms is also available. For example, the comparison of nucleotide sequences can be performed with the BLASTN program, score=100, wordlength=12. The comparison of amino acid sequences can be performed with the BLASTX program, score=50, word-length=3. For the remaining parameters of the BLAST programs, the default parameters can be used.

In many countries the use of genetically modified organisms (GMOs) for fermented milk products is not accepted. The present invention instead provides for a method of obtaining naturally occurring or induced mutant strains which can provide a desirable accumulation of glucose in the fermented milk product.

Thus, in a much preferred embodiment of the present invention the mutant strain is a naturally occurring mutant or an induced mutant.

A "mutant bacterium" or a "mutant strain" as used herein refers to a natural (spontaneous, naturally occurring) mutant bacterium or an induced mutant bacterium comprising one or more mutations in its genome (DNA) which are absent in the wild type DNA. An "induced mutant" is a bacterium where the mutation was induced by human treatment, such as treatment with chemical mutagens, UV- or gamma radiation etc. In contrast, a "spontaneous mutant" or "naturally occurring mutant" has not been mutagenized by man. Mutant bacteria are herein, non-GMO (non-genetically modified organism), i.e. not modified by recombinant DNA technology.

"Wild type strain" refers to the non-mutated form of a bacterium, as found in nature.

Terms such as "strains with a sweetening property", "strains which can provide a desirable accumulation of glucose in the fermented milk product" and "strains with enhanced properties for natural sweetening of food products" are used interchangeably herein to characterize an advantageous aspect of using the strains of the present invention in fermentation of milk products.

In a preferred embodiment, the mutant strain of *Streptococcus thermophilus* according to the invention increases the amount of glucose in 9.5% B-milk to at least 5 mg/mL when inoculated into the 9.5% B-milk at a concentration of $10^6$-$10^7$ CFU/ml and grown at 40° C. for at least 20 hours.

In another preferred embodiment, the mutant strain of *Streptococcus thermophilus* according to the invention increases the amount of glucose in 9.5% B-milk with 0.05% sucrose to at least 5 mg/mL when inoculated into the 9.5% B-milk with 0.05% sucrose at a concentration of $10^6$-$10^7$ CFU/ml and grown at 40° C. for at least 20 hours.

In the present context, 9.5% B-milk is boiled milk made with reconstituted low fat skim milk powder to a level of dry matter of 9.5% and pasteurized at 99° C. for 30 min. followed by cooling to 40° C.

In more preferred embodiments of the invention the mutant strain leads to an increase in the amount of glucose to at least 6 mg/mL, such as at least 7 mg/mL, such as at least 8 mg/mL, such as at least 9 mg/ml, such as at least 10 mg/ml, such as at least 11 mg/ml, such as at least 12 mg/ml, such as at least 13 mg/ml, such as at least 14 mg/ml, such as at least 15 mg/ml, such as at least 20 mg/ml, such as at least 25 mg/ml.

In another embodiment of the invention the mutant strain of *Streptococcus thermophilus* is resistant to 2-deoxyglucose.

The term "resistant to 2-deoxyglucose" herein is defined by that a particular mutated bacterial strain has the ability to grow to a colony when streaked on a plate of M17 medium containing 20 mM 2-deoxyglucose after incubation at 40° C. for 20 hours. The presence of 2-deoxygluxcose in the culture medium will prevent the growth of non-mutated strains while the growth of the mutated strains is not affected or not affected significantly. Non-mutated strains which can be used as sensitive reference strains in the assessment of resistance preferably include the strains CHCC14994 and CHCC11976.

Examples 1 and 2 herein exemplify the isolation of mutant strains of *Streptococcus thermophilus* which are resistant to 2-deoxyglucose.

In yet another embodiment, the mutant strain according to the invention can be characterized by its growth pattern. This is illustrated by the finding that the growth rate of the mutant strain is higher in M17 medium+2% galactose than in M17 medium+2% glucose. The growth rate is measured as the development in optical density of the exponentially growing culture at 600 nanometers ($OD_{600}$) with time as described in Example 2 herein.

In a preferred embodiment the growth rate is at least 5% higher, such as at least 10% higher, such as at least 15% higher, such as at least 20% higher, in M17 medium+2% galactose than in M17 medium+2% glucose.

In a preferred embodiment the mutation results in the replacement of the codon coding for serine with the codon coding for proline in position 72 in SEQ ID NO. 2. Preferably the mutation in the glcK gene results in the replacement of a T with a C on position 214 in SEQ ID NO. 1.

In another preferred embodiment the mutation results in the replacement of the codon coding for threonine with the codon coding for isoleucine in position 141 in SEQ ID NO. 2.

Preferably, the mutation in the glcK gene results in the replacement of a C with a T on position 422 in SEQ ID NO. 1.

It should be emphasized that the glcK gene of a *Streptococcus thermophilus* may be inactivated by other types of mutations in other sites of the glcK gene.

In a preferred embodiment the *Streptococcus thermophilus* strain carries a mutation that reduces the transport of glucose into the cell.

The term "a mutation that reduces the transport of glucose into the cell" as used herein refers to a mutation in a gene encoding a protein involved in transport of glucose which results in an accumulation of glucose in the environment of the cell. The level of glucose in the culture medium of a *Streptococcus thermophilus* strain can readily be measured by methods known to the skilled person and as described in Example 4 herein also when the culture medium is a milk substrate.

In preferred embodiments the mutation reduces the transport of glucose into the cell with at least 50%, such as at least 60%, such as at least 70%, such as at least 80%, such as at least 90%.

The transport of glucose into the cell can be determined by the glucose uptake assay as described by Cochu et al. (2003. Appl Environ Microbiol 69(9); 5423-5432).

Preferably, the *Streptococcus thermophilus* strain carries a mutation in a gene encoding a component of a glucose transporter, wherein the mutation inactivates the glucose transporter protein or has a negative effect on expression of the gene.

Figure 3:
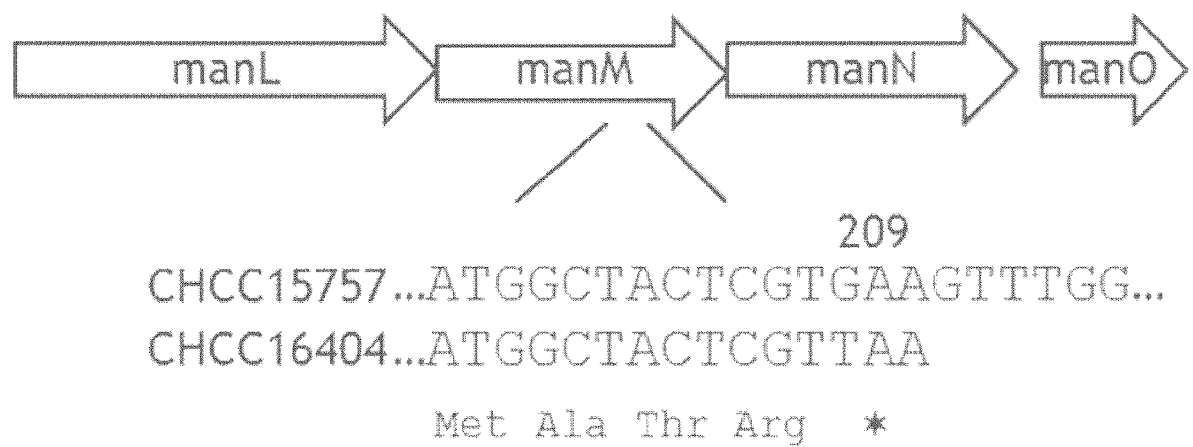
FIG. 3 depicts the man operon encoding the glucose/mannose phosphotransferase system (PTS) in *Streptococcus thermophilus*. When compared to the mother strain, CHCC15757, the hyper-lactose fermenting and glucose secreting mutant CHCC16404 was found to have a mutation in the manM gene encoding the $IIC^{Man}$ protein of the glucose/mannose PTS. The G to T mutation changes the GAA codon for glutamic acid at amino acid position 209 to a TAA stop codon (*) aborting translation in CHCC16404 and inactivating the function of the protein.

The component may be any component of a glucose transporter protein which is critical for the transport of glucose. E.g., it is contemplated that inactivation of any component of the glucose/mannose PTS in *Streptococcus thermophilus* depicted in FIG. 3 will result in inactivation of the glucose transporter function.

The term "the mutation inactivates the glucose transporter" as used herein refers to a mutation which results in an "inactivated glucose transporter", a glucose transporter protein which, if present in a cell, is not able to exert its normal function as well as mutations which prevent the formation of the glucose transporter protein or result in degradation of the glucose transporter protein.

In particular, an Inactivated glucose transporter protein is a protein which compared to a functional glucose transporter protein is not able to facilitate transport of glucose over a plasma membrane or facilitates transport of glucose over a plasma membrane at a significantly reduced rate. The gene encoding such an inactivated glucose transporter protein compared to the gene encoding a functional glucose transporter protein comprises a mutation in the open reading frame (ORF) of the gene, wherein said mutation may include, but is not limited to, a deletion, a frameshift mutation, introduction of a stop codon or a mutation which results in an amino acid substitution, which changes the functional properties of the protein, or a promoter mutation that reduces or abolishes transcription or translation of the gene.

In preferred embodiments the mutation reduces the activity (the rate of transport of glucose) of the glucose transporter protein by at least 50%, such as at least 60%, such as at least 70%, such as at least 80%, such as at least 90%.

The glucose transporter activity can be determined by the glucose uptake assay as described by Cochu et al. (2003. Appl Environ Microbiol 69(9); 5423-5432).

The term "functional glucose transporter protein" as used herein refers to a glucose transporter protein which, if present in a cell, facilitates transport of glucose over a plasma membrane.

More preferred the *Streptococcus thermophilus* strain carries a mutation in the DNA sequence of the manM gene encoding the $IIC^{Man}$ protein of the glucose/mannose phosphotransferase system, wherein the mutation inactivates the $IIC^{Man}$ protein or has a negative effect on expression of the gene.

In an even more preferred embodiment the mutation results in the replacement of the codon coding for glutamic acid with a stop codon in position 209 of SEQ ID NO. 6 of the $IIC^{Man}$ protein of the glucose/mannose phosphotransferase system. Preferably, the mutation results in the replacement of a G with a T in position 625 of SEQ ID NO. 5.

A second aspect of the invention relates to a *Streptococcus thermophilus* strain selected from the group consisting of the *Streptococcus thermophilus* CHCC15757 strain that was deposited at Deutsche Sammlung von Mikroorganismen und Zellkulturen under accession No. DSM 25850, a *Streptococcus thermophilus* CHCC15887 strain that was deposited at Deutsche Sammlung von Mikroorganismen und Zellkulturen under accession No. DSM 25851, the *Streptococcus thermophilus* CHCC16404 strain that was deposited at Deutsche Sammlung von Mikroorganismen und Zellkulturen under accession No. DSM 26722 and strains derived therefrom.

In the present context, the term "strains derived therefrom" should be understood as strains derived, or strains which can be derived from a strain (or their mother strain) of the invention by means of e.g. genetic engineering, radiation and/or chemical treatment. The "strains derived therefrom" can also be spontaneously occurring mutants. It is preferred that the "strains derived therefrom" are functionally equivalent mutants, e.g. mutants that have substantially the same, or improved, properties (e.g. regarding excretion of glucose) as their mother strain. Such "strains derived therefrom" are part of the present invention. Especially, the term "strains derived therefrom" refers to strains obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood as one mutagenization step followed by a screening/selection step), but it is presently preferred that no more than 20, or no more than 10, or no more than 5, treatments (or screening/selection steps) are carried out. In a presently preferred mutant less than 1%, less than 0.1%, less than 0.01%, less than 0.001% or even less than 0.0001% of the nucleotides in the bacterial genome have been replaced with another nucleotide, or deleted, compared to the mother strain.

Accordingly, in a preferred embodiment the *Streptococcus thermophilus* strain is selected from the group consisting of the *Streptococcus thermophilus* CHCC15757 strain that was deposited at Deutsche Sammlung von Mikroorganismen und Zellkulturen under accession No. DSM 25850, a *Streptococcus thermophilus* CHCC15887 strain that was deposited at Deutsche Sammlung von Mikroorganismen und Zellkulturen under accession No. DSM 25851, the *Streptococcus thermophilus* CHCC16404 strain that was deposited at Deutsche Sammlung von Mikroorganismen und Zellkulturen under accession No. DSM 26722 and a mutant strain derived therefrom, wherein the mutant strain is obtained by using one of the deposited strains as starting material, and wherein the mutant has retained or further improved the lactose fermenting property and/or the glucose secreting property of said deposited strain.

*Lactobacillus delbrueckii* subsp. *bulgaricus* is a lactic acid bacterium which is frequently employed for commercial milk fermentation where the organism is normally used as part of a mixed starter culture.

Lactose is fermented more readily than the monosaccharides glucose, fructose, and mannose by *Lactobacillus delbrueckii* subsp. *bulgaricus* and strains of this species normally do not grow on galactose (Buchanan R. E., Gibbons N. E., eds (1974): Bergey's manual of determinative bacteriology (The Williams & Wilkins Co. Baltimore, Md.), 8th ed.). During fermentation of lactose by *Lactobacillus delbrueckii* subsp. *bulgaricus*, only the glucose portion of the lactose molecule is fermented and thus galactose accumulates in fermented milk products.

In order to obtain *Lactobacillus delbrueckii* subsp. *bulgaricus* strains which are unable to grow on glucose as carbon source, the present inventors have exposed strains of *Lactobacillus delbrueckii* subsp. *bulgaricus* to 2-deoxyglucose. The isolated mutants were resistant to 2-deoxyglucose and capable of growing in a milk substrate without using glucose as a carbon source. The mutants were found to increase the glucose content of milk. Accordingly, fermented milk products produced by use of these strains are characterized by a higher amount of glucose which renders the products sweeter in taste.

Surprisingly, the *Lactobacillus delbrueckii* subsp. *bulgaricus* strains of the invention alone are still fully capable of acidifying milk although acidification time to pH 5 is delayed by 2-5 hours. Additionally, as demonstrated in the Examples, it was found that the strains excreted approximately 5 mg/ml or more glucose while less than approximately 10 mg/ml lactose remained in the fermented milk when 9.5% B-milk was inoculated with $10^6$-$10^7$ CFU/ml of a *Lactobacillus delbrueckii* subsp. *bulgaricus* strain according to the invention and fermented with the *Lactobacillus delbrueckii* subsp. *bulgaricus* strain according to the invention at 40° C. for at least 20 hours. Therefore, the use of such strains for producing fermented milk products may have an importance for people with lactose intolerance.

Consequently, the final fermented milk has a higher inner sweetness index of approximately 2 or higher calculated as described by Godshall (1988. Food Technology 42(11):71-78), such as 2.5 or higher or such as 3 or higher.

The third aspect of the present invention relates to a *Lactobacillus delbrueckii* subsp. *bulgaricus* strain, wherein said strain is resistant to 2-deoxyglucose.

The term "resistant to 2-deoxyglucose" in relation to a *Lactobacillus delbrueckii* subsp. *bulgaricus* strain is defined by that a particular bacterial strain has the ability to grow to a colony after incubation at 40° C. for 20 hours when streaked on a plate of MRS-IM medium containing 2% lactose and 20 mM 2-deoxyglucose. The presence of 2-deoxyglucose in the culture medium will prevent the growth of non-resistant strains while the growth of resistant strains is not affected or not affected significantly. Non-resistant *Lactobacillus delbrueckii* subsp. *bulgaricus* strains which can be used as sensitive reference strains in the assessment of resistance include the *Lactobacillus delbrueckii* subsp. *bulgaricus* strains CHCC759, that was deposited at Deutsche Sammlung von Mikroorganismen und Zellkulturen (DSMZ) under the accession no. DSM 26419 and CHCC10019, that was deposited Deutsche Sammlung von Mikroorganismen und Zellkulturen (DSMZ) under the accession no. DSM 19252.

In the event the MRS-IM agar plates containing 2% lactose and furthermore containing 20 mM 2-deoxyglucose plate is overgrown with colonies, it is appropriate to increase the concentration of 2-deoxyglucose in the plates, for example to 30 mM or even 40 mM or higher. In the event no colonies are obtained, it is appropriate to decrease the concentration of 2-deoxyglucose in the plates, for example to 15 mM or 10 mM or even lower. If considered necessary, the mutation rate can be enhanced by using appropriate physical or chemical mutagenesis protocols.

Preferably, the *Lactobacillus delbrueckii* subsp. *bulgaricus* strain of the invention increases the amount of glucose in 9.5% B-milk to at least 5 mg/ml when inoculated into the 9.5% B-milk at a concentration of $10^6$ to $10^7$ CFU/ml and grown at 40° C. for at least 20 hours, such as for between 20 to 30 hours, such as for 20 hours.

In more preferred embodiments of the invention the mutant strain leads to an increase in the amount of glucose to at least 6 mg/mL, such as at least 7 mg/mL, such as at least 8 mg/mL, such as at least 9 mg/ml, such as at least 10 mg/ml, such as at least 11 mg/ml, such as at least 12 mg/ml, such as at least 13 mg/ml, such as at least 14 mg/ml, such as at least 15 mg/ml.

A fourth aspect of the Invention relates to a *Lactobacillus delbrueckii* subsp. *bulgaricus* strain which is selected from the group consisting of the *Lactobacillus delbrueckii* subsp. *bulgaricus* strain CHCC16159, that was deposited at Deutsche Sammlung von Mikroorganismen und Zellkulturen (DSMZ) under accession no. DSM26420, the *Lactobacillus delbrueckii* subsp. *bulgaricus* strain CHCC16160, that was deposited at Deutsche Sammlung von Mikroorganismen und Zellkulturen (DSMZ) under accession no. DSM26421, and strains derived therefrom.

The term "strains derived therefrom" should be understood as defined above.

Accordingly, in a preferred embodiment the *Lactobacillus delbrueckii* subsp. *bulgaricus* strain is selected from the group consisting of the *Lactobacillus delbrueckii* subsp. *bulgaricus* strain CHCC16159, that was deposited at Deutsche Sammlung von Mikroorganismen und Zellkulturen (DSMZ) under accession no. DSM26420, the *Lactobacillus delbrueckii* subsp. *bulgaricus* strain CHCC16160, that was deposited at Deutsche Sammlung von Mikroorganismen und Zellkulturen (DSMZ) under accession no. DSM26421 and a mutant strain derived therefrom, wherein the mutant strain is obtained by using one of the deposited strains as starting material, and wherein the mutant has retained or further improved the lactose fermenting property and/or the glucose secreting property of said deposited strain.

A fifth aspect of the present invention relates to a composition comprising from $10^4$ to $10^{12}$ CFU (colony forming units)/g of a *Streptococcus thermophilus* strain according to the first or second aspect of the invention, such as from $10^5$ to $10^{11}$ CFU/g, such as from $10^6$ to $10^{10}$ CFU/g, or such as from $10^7$ to $10^9$ CFU/g of the *Streptococcus thermophilus* strain.

In a preferred embodiment the *Streptococcus thermophilus* strain is unable to acidify 9.5% B-milk, defined as resulting in a pH decrease of less than 1.0 when 9.5% B-milk is inoculated with $10^6$-$10^7$ CFU/ml of the *Streptococcus thermophilus* strain and incubated for 14 hours at 40° C., and the composition further comprises an amount of a compound, which can trigger acidification of the 9.5% B-milk by the *Streptococcus thermophilus* strain CHCC16404 that was deposited at Deutsche Sammlung von Mikroorganismen und Zellkulturen under accession No. DSM 26722, defined as resulting in a pH decrease of 1.0 or more when 9.5% B-milk is inoculated with $10^6$-$10^7$ CFU/ml of the *Streptococcus thermophilus* strain and incubated for 14 hours at 40° C.

Preferably, the compound is sucrose.

Preferably, the amount of sucrose is from 0.000001% to 2%, such as from 0.00001% to 0.2%, such as from 0.0001% to 0.1%, such as from 0.001% to 0.05%.

In an especially preferred embodiment the composition further comprises from $10^4$ to $10^{12}$ CFU/g of a *Lactobacillus delbrueckii* subsp. *bulgaricus* strain according to the invention, such as from $10^5$ to $10^{11}$ CFU/g, such as from $10^6$ to $10^{10}$ to CFU/g, or such as from $10^7$ to $10^9$ CFU/g of the *Lactobacillus delbrueckii* subsp. *bulgaricus* strain.

A preferred composition of the present invention comprises, for example, *Lactobacillus delbrueckii* subsp. *bulgaricus* strain CHCC16159 and/or *Lactobacillus delbrueckii* subsp. *bulgaricus* strain CHCC16160 in combination with *Streptococcus thermophilus* strain CHCC15757. A further preferred composition comprises *Lactobacillus delbrueckii* subsp. *bulgaricus* strain CHCC16159 and/or *Lactobacillus delbrueckii* subsp. *bulgaricus* CHCC16150 in combination with *Streptococcus thermophilus* strain CHCC15887. An even further preferred composition comprises *Lactobacillus delbrueckii* subsp. *bulgaricus* strain CHCC16159 and/or

*Lactobacillus delbrueckii* subsp. *bulgaricus* CHCC16150 in combination with *Streptococcus thermophilus* strain CHCC16404.

*Lactobacillus delbrueckii* subsp. *bulgaricus*, *Streptococcus thermophilus* and other lactic acid bacteria are commonly used as starter cultures serving a technological purpose in the production of various foods, such as in the dairy industry, such as for fermented milk products. Thus, in another preferred embodiment the composition is suitable as a starter culture.

Starter cultures may be provided as frozen or dried starter cultures in addition to liquid starter cultures. Thus, in yet another preferred embodiment the composition is in frozen, freeze-dried or liquid form.

As disclosed in WO 2005/003327, it is beneficial to add certain cryoprotective agents to a starter culture. Thus, a starter culture composition according to the present invention may comprise one or more cryoprotective agent(s) selected from the group consisting of inosine-5'-monophosphate (IMP), adenosine-5'-monophosphate (AMP), guanosine-5'-nonophosphate (GMP), uranosine-5'-monophosphate (UMP), cytidine-5'-monophosphate (CMP), adenine, guanine, uracil, cytosine, adenosine, guanosine, uridine, cytidine, hypoxanthine, xanthine, hypoxanthine, orotidine, thymidine, inosine and a derivative of any such compounds.

A sixth aspect of the invention is directed to a method for producing a fermented milk product comprising inoculating and fermenting a milk substrate with at least one *Streptococcus thermophilus* strain according to the first or second aspect of the present invention.

The term "milk" is to be understood as the lacteal secretion obtained by milking any mammal, such as a cow, a sheep, a goat, a buffalo or a camel. In a preferred embodiment, the milk is cow's milk.

The term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder.

Preferably, at least part of the protein in the milk substrate is proteins naturally occurring in milk, such as casein or whey protein. However, part of the protein may be proteins which are not naturally occurring in milk.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

"Fermentation" in the methods of the present invention means the conversion of carbohydrates into alcohols or acids through the action of a microorganism. Preferably, fermentation in the methods of the invention comprises conversion of lactose to lactic acid.

Fermentation processes to be used in production of fermented milk products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a dairy product in solid or liquid form (fermented milk product).

The term "fermented milk product" as used herein refers to a food or feed product wherein the preparation of the food or feed product involves fermentation of a milk substrate with a lactic acid bacteria. "Fermented milk product" as used herein includes but is not limited to products such as yoghurt, cheese, sour cream and buttermilk as well as fermented whey.

In a preferred embodiment the concentration of *Streptococcus thermophilus* cells inoculated is from $10^4$ to $10^9$ CFU *Streptococcus thermophilus* cells per ml of milk substrate, such as from $10^4$ CFU to $10^8$ CFU *Streptococcus thermophilus* cells per ml of milk substrate.

In another preferred embodiment the *Streptococcus thermophilus* strain is unable to acidify the 9.5% B-milk, defined as resulting in a pH decrease of less than 1.0 when 9.5% B-milk is inoculated with $10^6$-$10^7$ CFU/ml of the *Streptococcus thermophilus* strain and incubated for 14 hours at 40° C., and the milk substrate is added an amount of a compound, effective to trigger acidification of 9.5% B-milk by the *Streptococcus thermophilus* strain CHCC16404 that was deposited at Deutsche Sammlung von Mikroorganismen und Zellkulturen under accession No. DSM 26722, defined as resulting in a pH decrease of 1.0 or more when 9.5% B-milk is inoculated with $10^6$-$10^7$ CFU/ml of the *Streptococcus thermophilus* strain and incubated for 14 hours at 40° C.

Preferably, the compound is sucrose.

Preferably, the amount of sucrose is from 0.000001% to 2%, such as from 0.00001% to 0.2%, such as from 0.0001% to 0.1%, such as from 0.001% to 0.05%.

A seventh aspect of the invention is directed to a method for producing a fermented milk product comprising inoculating and fermenting a milk substrate with at least one *Lactobacillus delbrueckii* subsp. *bulgaricus* strain according to the third or fourth aspect of the present invention.

In a preferred embodiment the concentration of *Lactobacillus delbrueckii* subsp. *bulgaricus* cells inoculated is from $10^4$ to $10^9$ CFU *Lactobacillus delbrueckii* subsp. *bulgaricus* cells per ml of milk substrate, such as from $10^4$ CFU to $10^8$ CFU *Lactobacillus delbrueckii* subsp. *bulgaricus* cells per ml of milk substrate.

In a preferred embodiment the method for producing the fermented milk product comprises inoculating and fermenting a milk substrate with at least one *Streptococcus thermophilus* strain according to the present invention and at least one *Lactobacillus delbrueckii* subsp. *bulgaricus* strain according to the present invention.

In another preferred embodiment the fermented milk product is a yoghurt or a cheese.

Examples of cheeses which are prepared by fermentation with *Streptococcus thermophilus* and *Lactobacillus delbrueckii* subsp. *bulgaricus* include Mozzarella and pizza cheese (Høier et al. (2010) in The Technology of Cheesemaking, $2^{nd}$ Ed. Blackwell Publishing, Oxford; 166-192).

Preferably the fermented milk product is a yoghurt.

In the present context, a yoghurt starter culture is a bacterial culture which comprises at least one *Lactobacillus delbrueckii* subsp *bulgaricus* strain and at least one *Streptococcus thermophilus* strain. In accordance herewith, the term "yoghurt" refers to a fermented milk product obtainable by inoculating and fermenting milk with a composition comprising a *Lactobacillus delbrueckii* subsp *bulgaricus* strain and a *Streptococcus thermophilus* strain.

In an eighth aspect the present invention relates to a fermented milk product obtainable by the method according the sixth or seventh aspect of the invention.

In a ninth aspect the present invention relates to a fermented milk product comprising at least one *Streptococcus thermophilus* strain according to the first or second aspect of the invention.

In a tenth aspect the present invention relates to a fermented milk product comprising at least one *Lactobacillus delbrueckii* subsp. *bulgaricus* strain according to the third or fourth aspect of the invention.

In a preferred embodiment the fermented milk product comprises at least one *Streptococcus thermophilus* strain according to the invention and at least one *Lactobacillus delbrueckii* subsp. *bulgaricus* strain according to the invention.

In another preferred embodiment the fermented milk product is a yoghurt or a cheese. Preferably, the fermented milk product is a yoghurt.

In an eleventh aspect the present invention relates to the use of a *Streptococcus thermophilus* strain according to the first or second aspect of the invention for the preparation of a fermented milk product.

In a twelfth aspect the present invention relates to the use of a *Lactobacillus delbrueckii* subsp. *bulgaricus* according to the third or fourth aspect of the invention for the preparation of a fermented milk product.

A thirteenth aspect of the present invention relates to the use of a *Streptococcus thermophilus* strain according to the invention and a *Lactobacillus delbrueckii* subsp. *bulgaricus* according to the invention for the preparation of a fermented milk product.

A fourteenth aspect relates to the use of a *Streptococcus thermophilus* strain according to the first or second aspect of the invention for increasing the sweetness of a fermented milk product.

In a fifteenth aspect the present invention is directed to the use of a *Lactobacillus delbrueckii* subsp. *bulgaricus* strain according to the third and fourth aspect of the invention for increasing the sweetness of a fermented milk product.

In a sixteenth aspect the present invention is directed to the use of a *Streptococcus thermophilus* strain according to the first or second aspect of the invention and a *Lactobacillus delbrueckii* subsp. *bulgaricus* strain according to the third and fourth aspect of the invention for increasing the sweetness of a fermented milk product.

Especially, children as a consumer group have a preference for sweet-tasting food products and it is contemplated that the *Streptococcus thermophilus* strain of the invention and the *Lactobacillus delbrueckii* subsp. *bulgaricus* strain of the invention may be particularly useful in increasing the sweetness of a fermented milk product intended for children.

A seventeenth aspect of the present invention relates to a fermented milk product according to the invention for use in reducing the calorie intake.

The fermented milk product according to the invention is thought to be especially useful in the diet of persons suffering from overweight or obesity.

Thus, in a preferred embodiment the fermented milk product according to the invention is for use in reducing the calorie intake of a person suffering from overweight or obesity.

Overweight and obesity are medical conditions defined by the World Health Organization (WHO) as abnormal or excessive fat accumulation that presents a risk to health. The Body Mass Index (BMI) can be used as a rough guide to classify overweight and obesity in adults and is calculated as a person's weight in kilograms divided by the square of his/her height in meters (kg/m$^2$). The WHO definition states that a BMI greater than or equal to 25 is overweight and that a BMI greater than or equal to 30 is obesity.

An eighteenth aspect of the present invention relates to the use of a *Streptococcus thermophilus* strain according to the first or second aspect of the invention for decreasing the lactose content in a fermented milk product.

In a nineteenth aspect the present invention is directed to the use of a *Lactobacillus delbrueckii* subsp. *bulgaricus* strain according to the third or fourth aspect of the invention for decreasing the lactose content in a fermented milk product.

A twentieth aspect of the present invention is related to the use of a *Streptococcus thermophilus* strain according to the first or second aspect of the invention and a *Lactobacillus delbrueckii* subsp. *bulgaricus* strain according to the third or fourth aspect of the invention for decreasing the lactose content in a fermented milk product.

A twenty-first aspect of the present invention is directed to a fermented milk product according to the invention for use in avoiding symptoms of lactose intolerance.

A twenty-second aspect relates to a composition of the invention for use as a medicament.

In a twenty-third aspect the invention is directed to the use of a *Streptococcus thermophilus* strain according to the invention for improving the growth of a *Bifidobacterium* strain.

In a preferred embodiment the *Bifidobacterium* strain belongs to a species selected from the group consisting of *Bifidobacterium longum*, *Bifidobacterium bifidum*, *Bifidobacterium lactis*, *Bifidobacterium brevis*, *Bifidobacterium animalis*, *Bifidobacterium adolescentis* and *Bifidobacterium infantis*, such as a strain selected from the group consisting of *Bifidobacterium animalis* subsp. *lactis* BB-12® strain deposited at Deutsche Sammlung von Mikroorganismen und Zellkulturen (DSMZ) under accession No. DSM 15954, *Bifidobacterium animalis* strain deposited at DSMZ under accession No. DSM 15954, *Bifidobacterium longum* subsp. *infantis* strain deposited at DSMZ under accession No. DSM 15953 and *Bifidobacterium longum* subsp. *longum* strain deposited at DSMZ under accession No. DSM 15955. Most preferred the *Bifidobacterium* strain is *Bifidobacterium animalis* subsp. *lactis* BB-12® deposited at DSMZ under accession No. DSM 15954.

In a twenty-fourth aspect the invention relates to the use of a *Lactobacillus delbrueckii* subsp. *bulgaricus* strain according to the invention for improving the growth of a *Bifidobacterium* strain.

In a preferred embodiment the *Bifidobacterium* strain belongs to a species selected from the group consisting of *Bifidobacterium longum*, *Bifidobacterium bifidum*, *Bifidobacterium lactis*, *Bifidobacterium brevis*, *Bifidobacterium animalis*, *Bifidobacterium adolescentis* and *Bifidobacterium infantis*, such as a strain selected from the group consisting of *Bifidobacterium animalis* subsp. *lactis* BB-12® strain deposited at Deutsche Sammlung von Mikroorganismen und Zellkulturen (DSMZ) under accession No. DSM 15954,

*Bifidobacterium animalis* strain deposited at DSMZ under accession No. DSM 15954. *Bifidobacterium longum* subsp. *infantis* strain deposited at DSMZ under access on No. DSM 15953 and *Bifidobacterium longum* subsp. *longum* strain deposited at DSMZ under accession No. DSM 15955. Most preferred the *Bifidobacterium* strain is *Bifidobacterium animalis* subsp. *lactis* BB-12® deposited at DSMZ under accession No. DSM 15954.

A twenty-fifth aspect relates to the use of a *Streptococcus thermophilus* strain according to the invention and a *Lactobacillus delbrueckii* subsp. *bulgaricus* strain according to the invention for improving the growth of *Bifidobacterium animalis* subsp. *lactis* strain BB-12® that was deposited at Deutsche Sammlung von Mikroorganismen und Zellkulturen under accession No. DSM 15954.

2-deoxyglucose and a determination of the growth pattern of the bacteria in M17 medium+2% galactose compared to in M17 medium+2% glucose is used for the selection of bacteria having a mutation in the glucokinase (glcK) gene.

In a twenty-sixth aspect of the present invention a method for screening and isolating a strain of *Streptococcus thermophilus* with a mutated glcK gene is provided. The method comprises the following steps:

a) providing a galactose-fermenting *Streptococcus thermophilus* mother strain;

b) selecting and isolating from a pool of mutant *Streptococcus thermophilus* strains derived from the mother strain a pool of mutant *Streptococcus thermophilus* strains which are resistant to 2-deoxyglucose; and c) selecting and isolating from the pool of mutant *Streptococcus thermophilus* strains which are resistant to 2-deoxyglucose a mutant *Streptococcus thermophilus* strain if the growth rate of the mutant *Streptococcus thermophilus* strain is higher in M17 medium+2% galactose than in M17 medium+2% glucose.

The term "resistant to 2-deoxyglucose" herein is defined by that a particular mutated bacterial strain has the ability to grow to a colony when streaked on a plate of M17 medium containing 2% lactose or 2% galactose and containing 20 mM 2-deoxyglucose after incubation at 40° C. or 20 hours. The presence of 2-deoxygluxcose in the culture medium will prevent the growth of non-mutated strains while the growth of the mutated strains is not affected or not affected significantly. Non-mutated strains which can be used as sensitive reference strains in the assessment of resistance include the strains CHCC14994 and CHCC11976.

Examples 1 and 2 herein exemplify the isolation of mutant strains of *Streptococcus thermophilus* which are resistant to 2-deoxyglucose.

In a preferred embodiment the method further comprises the step a1) subjecting the mother strain to mutagenization, such as subjecting the mother strain to a chemical and/or a physical mutagen.

In another preferred embodiment the method further comprises a step d) selecting and isolating from a pool of 2-deoxyglucose resistant *Streptococcus thermophilus* strains derived from the *Streptococcus thermophilus* strain selected in step c) a *Streptococcus thermophilus* strain if the growth rate of the *Streptococcus thermophilus* strain is high in M17 medium+2% sucrose but zero or at least 0-50% reduced compared to the growth rate of the mother strain in M17 medium+2% glucose.

The galactose-fermenting *Streptococcus thermophilus* mother strains are capable of growth on/in M17 medium+ 2% galactose and are defined herein by that they have the ability to lower the pH in M17 broth containing 2% galactose as sole carbohydrate to 5.5 or lower when inoculated from an overnight culture at 1% and incubated for 24 hours at 37° C. Such galactose-positive strains have been described in the prior art and WO2011/026863 (Chr. Hansen A/S) describes a method for obtaining such strains.

In a much preferred embodiment the mother strain is selected from the group consisting of the *Streptococcus thermophilus* CHCC14994 strain that was deposited at Deutsche Sammlung von Mikroorganismen und Zellkulturen under accession No. DSM 25838, the *Streptococcus thermophilus* CHCC11976 strain that was deposited at Deutsche Sammlung von Mikroorganismen und Zellkulturen under accession No. DSM 22934, and strains derived therefrom.

In the present context, the term "strains derived therefrom" should be understood as strains derived, or strains which can be derived from galactose-fermenting *Streptococcus thermophilus* mother strains by means of e.g. genetic engineering, radiation and/or chemical treatment. The "strains derived therefrom" can also be spontaneously occurring mutants. It is preferred that the "strains derived therefrom" are functionally equivalent mutants, e.g. mutants that have substantially the same, or improved, properties (e.g regarding fermentation of galactose) as their mother strain. Such "strains derived therefrom" are part of the present invention. Especially, the term "strains derived therefrom" refers to strains obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant less than 1%, less than 0.1%, less than 0.01%, less than 0.001% or even less than 0.0001% of the nucleotides in the bacterial genome have been replaced with another nucleotide, or deleted, compared to the mother strain.

In a twenty-seventh aspect a mutant *Streptococcus thermophilus* strain obtainable by the method according to the twenty seventh aspect is comprised herein.

In a twenty-eighth aspect of the present invention a method for screening and isolating a strain of *Lactobacillus delbrueckii* subsp. *bulgaricus* with an impaired glucose metabolism is provided. The method comprises the following steps:

a) providing a *Lactobacillus delbrueckii* subsp. *bulgaricus* mother strain;

b) selecting and isolating from a pool of mutant *Lactobacillus delbrueckii* subsp. *bulgaricus* strains derived from the mother strain a pool of *Lactobacillus delbrueckii* subsp. *bulgaricus* strains which are resistant to 2-deoxyglucose; and c) selecting and isolating from the pool of *Lactobacillus delbrueckii* subsp. *bulgaricus* strains which are resistant to 2-deoxyglucose a *Lactobacillus delbrueckii* subsp. *bulgaricus* strain if the growth rate of the *Lactobacillus delbrueckii* subsp. *bulgaricus* strain is higher in MRS-IM medium+2% lactose than in MRS-IM medium+2% glucose.

The isolation of mutant strains of *Lactobacillus delbrueckii* subsp. *bulgaricus* strains which are resistant to 2-deoxyglucose is described in detail in the Examples. Based on the 2-deoxyglucose resistance selection assay of Example 5, the skilled person can routinely test for a specific strain of interest (e.g. one from a relevant commercial product) if this specific strain of interest has the herein relevant resistance to 2-deoxyglucose. Based on the 2-deoxyglucose resistance mutant growth pattern of Example 6 the skilled person can routinely test for a specific strain of interest (e.g. one from a relevant commercial product) if this specific strain of interest has the relevant growth pattern which is a property of the selected mutants.

In a preferred embodiment the method further comprises the step a1) subjecting the mother strain to mutagenization, such as subjecting the mother strain to a chemical and/or a physical mutagen.

The *Lactobacillus delbrueckii* subsp. *bulgaricus* mother strains are capable of growing on/in MRS-IM medium+2% lactose and are defined herein by that they have the ability to lower the pH in MRS-IM broth containing 2% lactose as sole carbohydrate to 5.5 or lower when inoculated from an overnight culture at 1% and incubated for 24 hours at 37° C.

In a much preferred embodiment the mother strain is selected from the group consisting of the *Lactobacillus delbrueckii* subsp. *bulgaricus* CHCC759 strain that was deposited at Deutsche Sammlung von Mikroorganismen und Zellkulturen under accession No. DSM 26419, the *Lactobacillus delbrueckii* subsp. *bulgaricus* CHCC10019 strain that was deposited at Deutsche Sammlung von Mikroorganismen und Zellkulturen under accession No. DSM 19252, and strains derived therefrom.

In a twenty-ninth aspect a *Lactobacillus delbrueckii* subsp. *bulgaricus* strain obtainable by the method according to the twenty-eighth aspect is comprised herein.

Embodiments of the present invention are described below, by way of non-limiting examples.

EXAMPLES

Materials and Methods
Medium:
For *Streptococcus thermophilus*, the medium used is the M17 medium known to persons skilled in the art.
The M17 agar medium has the following composition per litre $H_2O$:
  agar, 12.75 g
  ascorbic acid, 0.5 g
  casein peptone (tryptic), 2.5 g
  disodium β-glycerophosphate pentahydrate, 19 g
  magnesium sulfate hydrate, 0.25 g
  meat extract, 5 g
  meat peptone (peptic), 2.5 g
  soyapeptone (papainic), 5 g
  yeast extract, 2.5 g
  final pH 7.1±0.2 (25° C.)
and M17 broth has the following composition per litre $H_2O$:
  ascorbic acid, 0.5 g
  magnesium sulfate, 0.25 g
  meat extract, 5 g
  meat peptone (peptic), 2.5 g
  sodium glycerophosphate, 19 g
  soya peptone (papainic), 5 g
  tryptone, 2.5 g
  yeast extract, 2.5 g
  final pH 7.0±0.2 (25° C.)
Carbon sources added are sterile lactose 20 g/l, glucose 20 g/l or galactose 20 g/l.

As known to the skilled person, the M17 medium is a medium that is considered to be suitable for growth of *Streptococcus thermophilus*. Further, as understood by the skilled person, in the present context, a M17 concentrate may be supplied from different suppliers and independently of the specific supplier one will (within standard measurement uncertainty) get the same herein relevant result of 2-deoxyglucose resistance for a herein relevant cell of interest.

The medium used for culturing *Lactobacillus delbrueckii* subsp. *bulgaricus* was MRS-IM medium. MRS-IM was used either in the form of agar plates or broth.

The MRS-IM agar medium had the following composition per litre $H_2O$:

| Tryptone | Oxoid L 42 | 10.0 g |
| Yeast extract | Oxoid L 21 | 5.0 g |
| Tween 80 | Merck nr 8.22187 | 1.0 g |
| $K_2HPO_4$ | Merck nr 105104 | 2.6 g |
| Na-acetate | Merck nr 106267 | 5.0 g |
| Diammonium-hydrogen-citrate | Merck nr 101154 | 2.0 g |
| $MgSO_4$, 7 $H_2O$ | Merck nr 105882 | 0.2 g |
| $MnSO_4$, $H_2O$ | Merck nr 105941 | 0.05 g |
| Agar | SO-BI-GEL | 13.0 g |

The pH was adjusted after autoclaving to 6.9±0.1 at 25° C.

The MRS-IM broth used in the below examples for liquid cultures had the following composition per litre $H_2O$:

| Tryptone | Oxoid L 42 | 10.0 g |
| Yeast extract | Oxoid L 21 | 5.0 g |
| Tween 80 | Merck nr 8.22187 | 1.0 g |
| $K_2HPO_4$ | Merck nr 105104 | 2.6 g |
| Na-acetate | Merck nr 106267 | 5.0 g |
| Diammonium-hydrogen-citrate | Merck nr 101154 | 2.0 g |
| $MgSO_4$, 7 $H_2O$ | Merck nr 105882 | 0.2 g |
| $MnSO_4$, $H_2O$ | Merck nr 105941 | 0.05 g |

The pH is adjusted after autoclaving to 6.9±0.1 at 25° C. The carbon sources, lactose 20 g/l or glucose 20 g/l, were first filtered sterile and then added to the autoclaved broth.

The above MRS-IM media can be varied to some extent without affecting the capability of the media to support growth of *Lactobacillus delbrueckii* subsp. *bulgaricus*. Further, as will be understood by the skilled person, a MRS-IM concentrate or the various components described above may be obtained from different suppliers and used for the preparation of a MRS-IM medium. These media will likewise be used in the below examples, in particular in the 2-deoxyglucose resistance selection assay.

Mother Strains
*Streptococcus thermophilus* CHCC11976 (galactose-fermenting strain with a mutation in the GalK gene and producing exopolysaccharides as described in WO 2011/026863).
*Streptococcus thermophilus* CHCC14994 (galactose-fermenting strain).
*Lactobacillus delbrueckii* subsp. *bulgaricus* CHCC759.
*Lactobacillus delbrueckii* subsp. *bulgaricus* CHCC10019.
2-deoxy-glucose Resistant Strains
*Streptococcus thermophilus* CHCC15757 (2-deoxyglucose resistant mutant of CHCC14994).
*Streptococcus thermophilus* CHCC15887 (2-deoxyglucose resistant mutant of CHCC11976).
*Streptococcus thermophilus* CHCC16404 (hyper-lactose fermenting and glucose secreting mutant of CHCC15757).
*Lactobacillus delbrueckii* subsp. *bulgaricus* CHCC16159 (2-deoxyglucose resistant mutant of CHCC759).

*Lactobacillus delbrueckii* subsp. *bulgaricus* CHCC16160 (2-deoxyglucose resistant mutant of CHCC10019).

Example 1

Use of 2-Deoxyglucose to Isolate Glucose Kinase Mutants of *Streptococcus thermophilus* with Enhanced Excretion of Glucose In order to isolate mutants of *Streptococcus thermophilus* strain CHCC11976 and of *Streptococcus thermophilus* strain CHCC14994, cells derived from the growth of a single colony were inoculated into 10 ml of M17 broth containing 2% lactose and grown overnight at 40° C.

Next day, the strains were plated in serial dilutions on M17 agar plates containing 2% galactose and a concentration of 2-deoxyglucose of either 20 mM (CHCC14994) or 30 mM (CHCC11976) and incubated for 20 hours at 40° C. Resistant colonies were at first re-streaked on the same type of agar plates as they were selected. Survivors were used to inoculate fresh M17 broth containing either 2% lactose, 2% galactose or 2% glucose and growth was measured.

From this, a number of mutants that ware able to grow faster on galactose than on glucose were identified as outlined in Example 2. Two such mutants were CHCC15757 and CHCC15887, which are derived from CHCC14994 and CHCC11976 respectively.

Example 2

2-Deoxyglucose Resistance Mutant Growth Pattern

To ensure the selection of 2-deoxyglucose resistant mutants that can grow on galactose, two strains that were selected from a galactose-fermenting strain collection were used. While these galactose-fermenting strains still grow at least 10% faster in exponential phase in M17 broth+2% glucose than in M17 broth+2% galactose, the 2-deoxyglucose resistant mutant derivates of CHCC11976 and CHCC14994, such as CHCC15757 and CHCC15887, on the other hand, are characterized by growing faster in exponential phase in M17 broth+2% galactose than in M17 broth+2% glucose.

Growth in exponential phase is herein measured as the development in optical density of the exponentially growing culture at 600 nanometers ($OD_{600}$) with time at 40° C.

As known by the skilled person, it may vary from species to species when the culture is in exponential growth. The skilled person will know how to determine the growth in exponential phase, e.g. between $OD_{600}$ 0.1-1.0.

The optical density (OD) of the culture is measured in a spectrophotometer.

Conclusion:
Based on the 2-deoxyglucose resistance mutant growth pattern of this Example 2—for a specific strain of interest (e.g. one from a relevant commercial product)—the skilled person can routinely test if this specific strain of interest has the herein relevant growth pattern which is a property of the selected mutants.

Example 3

Mutation Analysis Assay of the Gene Encoding Glucose Kinase

Total DNA was isolated from the mutants identified in Example 1 to perform mutation analysis assay of the gene encoding glucose kinase. Sequencing of the glucose kinase gene revealed that the gene in CHCC15757 contains a non-conserved mutation in codon 141 generating an isoleucine instead of a threonine codon. Sequencing of the gene from mutant CHCC15887 revealed a mutation in codon 72 resulting in a non-conserved amino acid change from serine to proline (FIG. 2)

The 2-deoxyglucose resistant strains complying to the conditions specified in Examples 1 and 2 and isolated as described in Example 1 are characterized by having a mutation in the gene encoding glucose kinase (glcK). The mutation can result in an amino acid change of the encoded enzyme or result in generation of a stop codon which will truncate the encoded enzyme.

To reveal the mutation in the glcK gene, the specific strain of interest is grown in the liquid broth (M17) to which is added 2% lactose at 40° C. over night. After isolation of the chromosomal DNA, the DNA was subjected to PCR analysis using two primers complementary to a conserved region just upstream and just downstream of the gene encoding glucose kinase. The sequences of the primers are:

```
GK1F:
                                      (SEQ ID NO. 3)
5' CTT GGG TAA AAG GCT CTA TG 3'

GK1R:
                                      (SEQ ID NO. 4)
5' CGT TTT TCA ACA AAA AAG TGC TACC 3'
```

The conditions for the PCR reactions were as specified by the manufacturer of the PCR amplification kit (ROCHE) e.g.
2 µl Chromosomal DNA
1 µl Primer GK1F
1 µl Primer GK1R
25 µl Master mix
21 µl H2O
PCR-program: (94° C.—1.5 min., 50° C.—1 min., 72° C.—1.5 min.)×30

PCR amplification generates a 1168 bp fragment. After purification using a PCR purification kit from Biorad, the PCR fragment was submitted for DNA sequencing at Macrogen using the same two primers that were used for the amplification. After sequencing, the DNA sequence was compared to that of the mother strain.

Example 4

Carbohydrate Analysis of Fermented Milk

In another experiment, the sugar concentrations of relevant sugar were determined in milk fermented with CHCC14994, CHCC11976, CHCC15757 and CHCC15887, respectively. 9.5% B-milk was inoculated with 1% ($10^6$-$10^7$ CFU/ml) of a culture grown over night in M17 broth to which is added 2% galactose. The acidification was followed with an INTAB PC logger and Easyview software. After 30 hours of acidification at 40° C. milk samples were taken for HPLC analysis to obtain the content of relevant sugars and acids. The acidification curves showed that the mutants had a slightly delayed initiation of acidification but ended at a similar end pH. The HPLC data is presented in Table 1.

From Table 1 it is apparent that the two glcK mutant strains, CHCC15757 and CHCC15887, consume at least 71% of the lactose, while the mother strains consume approximately 28% of the lactose. For the most lactose fermenting mutant, CHCC15887, as little as 11.9 mg/ml remains in the fermented milk indicating a role for this product even for people with lactose intolerance. Very significantly, the two glcK mutants have excreted between 8.3 and 11.3 mg/ml of glucose while the glucose secretion of the mother strains is below detection level. At the same time both mutant strains also secrete more galactose than the mother strains: between 34 and 52%. Taking into account that sucrose is a 100 reference, and the sweetness of lactose is 16, the sweetness of galactose is 32 and the sweetness of glucose is 74.3, a calculation of the relative sweetness of the final fermented product suggests a sweetness 2.0 times sweeter when fermented with the best mutant CHCC15757 than with the corresponding mother strain CHCC14994.

TABLE 1

HPLC data of milk samples.

| Sample No. | Amount mg/ml Citric acid | Amount mg/ml Lactic acid | Amount mg/ml Acetic acid | Amount mg/ml Galactose | Amount mg/ml Glucose | Amount mg/ml Lactose | Amount mg/ml Fructose | Sweetness |
|---|---|---|---|---|---|---|---|---|
| Detection limit | <1.25 | <1.25 | <1.25 | <1.5 | <1.5 | <1.5 | <1.5 | |
| Milk | 1.8 | 1.7 | <1.25 | <1.5 | <1.5 | 47.6 | <1.5 | 761.6 |
| CHCC11976 | 2.0 | 8.2 | <1.25 | 7.2 | <1.5 | 34.4 | <1.5 | 781 |
| CHCC15887 | 1.8 | 7.8 | <1.25 | 10.9 | 8.3 | 11.9 | <1.5 | 1156 |
| CHCC14994 | 1.8 | 7.2 | <1.25 | 4.9 | <1.5 | 34.3 | <1.5 | 705.6 |
| CHCC15757 | 1.7 | 7.1 | <1.25 | 10.3 | 11.3 | 13.8 | <1.5 | 1390 |

Sweetness calculated: mg/ml glucose *74 + mg/ml lactose *16 + mg/ml galactose * 32.

As the two glcK mutant strains, CHCC15757 and CHCC15887, excrete high levels of glucose, it is contemplated that the mutations in the glcK gene inactivates the the encoded glucokinase protein.

Example 5

Selection of 2-Deoxyglucose Resistant Lactobacillus delbrueckii subsp. bulgaricus Strains Selection of 2-deoxyglucose Resistant Mutants Two Lactobacillus delbrueckii subsp. bulgaricus strains of interest, CHCC759 and CHCC10019, were independently from one another inoculated into 10 ml of the above-described MRS-IM broth containing 2% lactose and incubated anaerobically at 40° C. overnight. In the next step, samples of these cultures containing about $3 \times 10^8$ cells were plated on MRS-IM agar plates containing 2% lactose and furthermore containing 20 mM 2-deoxyglucose. Colonies arising on the plates were purified by single colony streaking on MRS-IM agar plates containing 2% lactose and furthermore containing 20 mM 2-deoxyglucose and further characterized as described below.

2-deoxyglucose Resistance Assay:

The following method is suitable for determining whether or not a strain of interest is resistant to 2-deoxyglucose. Strains of interest are inoculated into 10 ml of the above-described MRS-IM broth containing 2% lactose and incubated anaerobically at 40° C. over night. In the next step, diluted samples of these cultures containing about $10^4$-$10^5$ cells are plated on MRS-IM agar plates containing 2% lactose and furthermore containing the same 2-deoxyglucose concentration that was used for selection of the resistant mutant (typically 20 mM but other concentrations might be used). The agar plates are incubated under anaerobic conditions for 20 hours at 40° C. and inspected. Lactobacillus delbrueckii subsp. bulgaricus strains which are not resistant to 2-deoxyglucose will produce few if any colonies whereas strains which are resistant to 2-deoxyglucose will produce a multitude of colonies. Appropriate controls include the Lactobacillus delbrueckii subsp. bulgaricus strains, CHCC759 and CHCC10019, which are sensitive to 2-deoxyglucose at a concentration of 20 mM and CHCC16159 and CHCC16160 which are resistant to 20 mM 2-deoxyglucose.

Result: Several clones that were capable of growing under the selective conditions in the presence of 2-dexyglucose were isolated by this approach. Mutant strains that showed a rapid growth on plates with 2-dexyglucose were designated CHCC16159 (derived from mother strain CHCC759) and CHCC16160 (derived from mother strain CHCC10019). These mutant strains were deposited at the Deutsche Sammlung von Mikroorganismen und Zellkulturen (DSMZ) GmbH.

Example 6

Growth Pattern of 2-Deoxyglucose Resistant Mutants of Lactobacillus delbrueckii subsp. bulgaricus To ensure that the 2-deoxyglucose resistant mutants of Lactobacillus delbrueckii subsp. bulgaricus have either lost the ability to grow on glucose or have an impaired ability to grow on glucose as carbon source, the growth pattern of the mutants was compared to that of the mother strains by growing both the mother strains, CHCC759 and CHCC10019, and the mutants, CHCC16159 and CHCC16160, in MRS-IM broth containing 2% glucose.

While the 2 mother strains, CHCC759 and CHCC10019, grew exponentially in MRS-IM broth added 2% glucose with a doubling time less than 10 hours, the two 2-deoxyglucose resistant mutants CHCC16159 and CHCC16160 did not grow or grew only very slowly in this medium. Growth in the exponential phase was monitored by measuring the optical density of the exponentially growing culture at 600 nanometers ($OD_{600}$) at 40° C. in a spectrophotometer. The exponential phase of growth was reached between $OD_{600}$ 0.1-1.0.

Example 7

Carbohydrate Analysis of Milk Fermented with Strains of Lactobacillus delbrueckii subsp. bulgaricus In another experiment, the sugar concentrations of different sugars were determined in milk fermented with the Lactobacillus delbrueckii subsp. bulgaricus strains CHCC759, CHCC10019, CHCC16159, and CHCC16160, respectively. 9.5% B-milk was inoculated with 1% ($10^6$-$10^7$ CFU/ml) of a liquid culture grown over night anaerobically in MRS-IM broth containing 2% lactose. The acidification was followed with an INTAB PC logger and the Easyview software. After 30 hours of acidification at 40° C., milk samples were taken for HPLC analysis to measure the amounts of various sugars and organic acids. The acidification curves showed that the mutants had a somewhat delayed initiation of acidification and ended at a slightly higher end pH. The HPLC data are presented in Table 2.

As can be seen from Table 2, the two 2-deoxyglucose resistant mutant strains, CHCC16159 and CHCC16160, consumed at least about 94% of the lactose, while the mother strains consumed at least about 37% of the lactose. For the mutant showing the highest production of lactic acid, CHCC16160, as little as 2.9 mg/ml lactose remained in the fermented milk. Fermented milk products with such low levels of lactose could be suitable for consumption by people with lactose intolerance.

Significantly, the two mutant strains, CHCC16159 and CHCC16160, excreted between 15.2 and 15.8 mg/ml of glucose while the glucose secretion of the mother strains is below detection level for CHCC10019 and 4.2 mg/ml for CHCC759, respectively. At the same time both mutant strains also secreted more galactose than the mother strains. If the reference value for sweetness of sucrose is 100, and the sweetness of lactose is 16, the sweetness of galactose is 32 and the sweetness of glucose is 74, a calculation of the relative sweetness of the final fermented product suggests that the mutant CHCC16160 produces a fermented milk product that is 2.5 times sweeter than with the corresponding mother strain CHCC10019.

used to inoculate fresh M17 broth containing either 2% lactose, 2% galactose, 2% sucrose or 2% glucose.

From this, we were able to isolate a mutant, CHCC16404, derived from CHCC15757, that was unable to grow h B-milk but able to grow in M17 added 2% sucrose at 40° C. Furthermore, CHCC16404 was unable to grow in M17 added 2% glucose.

Growth in exponential phase is herein measured as the development in optical density of the exponentially growing culture at 600 nanometers ($OD_{600}$) with time at 40° C.

Example 9

Growth Pattern of Hyper-Lactose Fermenting and Glucose Secreting Streptococcus thermophilus Mutant CHCC16404

To ensure maintenance and proper growth of mutant CHCC16404, the strain was grown at 40° C. in M17 added 2% sucrose. To our surprise, we observed that mutant strain CHCC16404 was able to acidify 9.5% B-milk only when the strain was inoculated with 1% ($10^6$-$10^7$ CFU/ml) of a culture grown over night in M17 broth added 2% sucrose or when the milk was added sucrose. We observed that addition of as little as 0.01% sucrose to the milk enabled CHCC16404 to acidify 9.5% B-milk. Furthermore, CHCC16404 was unable to grow in M17 added 2% glucose at 40° C. as opposed to the mother strain CHCC15757 that can grow in M17 added glucose under the same conditions. Together these results indicated that the 2-deoxyglucose treatment of CHCC15757, that generated CHCC16404, has selected a mutation that inactivates the glucose uptake system disabling uptake of secreted glucose from the medium

TABLE 2

HPLC data of milk samples.

| Sample No. | Amount mg/ml Citric acid | Amount mg/ml Lactic acid | Amount mg/ml Acetic acid | Amount mg/ml Galactose | Amount mg/ml Glucose | Amount mg/ml Lactose | Amount mg/ml Fructose | Sweetness |
|---|---|---|---|---|---|---|---|---|
| Detection limit | <1.25 | <1.25 | <1.25 | <1.5 | <1.5 | <1.5 | <1.5 | |
| Milk | 1.9 | <1.25 | <1.25 | <1.5 | <1.5 | 55.5 | <1.5 | 888 |
| CHCC759 | 1.8 | 9.6 | <1.25 | 13.1 | 4.2 | 18.1 | <1.5 | 1021 |
| CHCC16159 | 2.0 | 7.9 | <1.25 | 21.4 | 15.2 | 1.7 | <1.5 | 1841 |
| CHCC10019 | 1.8 | 11.1 | <1.25 | 12.4 | >1.5 | 20.8 | <1.5 | 730 |
| CHCC16160 | 1.9 | 5.4 | <1.25 | 19.4 | 15.8 | 2.9 | <1.5 | 1841 |

Sweetness calculated: mg/ml glucose *74 + mg/ml lactose *16 + mg/ml galactose * 32.

Example 8

Selection of a Hyper-Lactose Fermenting and Glucose Secreting Mutant of Streptococcus thermophius In order to isolate a hyper-lactose fermenting and glucose secreting mutant of Streptococcus thermophilus strain CHCC15757, cells derived from the growth of a single colony were inoculated into 10 ml of M17 broth containing 2% galactose and grown overnight at 40° C.

Next day, the strain was plated in serial dilutions on M17 agar plates containing 2% galactose and a concentration of 2-deoxyglucose of 30 mM and incubated for 20 hours at 40° C. Resistant colonies were at first re-streaked on the same type of agar plates as they were selected. Survivors were Example 10

Carbohydrate Analysis of Milk Fermented with Hyper-Lactose Fermenting and Glucose Secreting Streptococcus thermophilus Mutant CHCC16404

In another experiment, the sugar concentrations of relevant sugars were determined in milk fermented with CHCC16404. Bottles containing 9.5% B-milk added 0.01%, 0.02%, 0.03% and 0.05% sucrose respectively were inoculated with 1% ($10^6$-$10^7$ CFU/ml) of a culture grown over night in M17 broth to which is added 2% sucrose. The acidification was followed with an INTAB PC logger and Easyview software. After 30 hours of acidification at 40° C., milk samples were taken for HPLC analysis to obtain the content of relevant sugars and acids.

From Table 3 it is apparent that the hyper-lactose fermenting and glucose secreting mutant CHCC16404, surprisingly, consumes all of the lactose at all concentrations of added sucrose tested in this experiment. We have also observed that when a higher sucrose concentration was added (e.g. >0.1 mg/ml), the lactose fermentation is not completed before the Final pH is reached. Furthermore Table 3 also shows that all the lactose is converted into glucose and galactose and that only part of the galactose is used for fermentation at all concentrations of added sucrose. Interestingly, the secreted glucose is not taken up again thereby leaving more than 23.9 mg/ml glucose in the milk. Since about 25% of the galactose is fermented more than 16 mg/ml of galactose remains in the milk after fermentation. These data indicate that CHCC16404, in addition to the glcK mutation inherited from the mother strain CHCC15757, also harbours a mutation that inactivates the glucose uptake system disabling uptake of secreted glucose from the medium. Comparison of the data in Table 3 with those in Table 1 and taking into account that sucrose is a 100 reference, and the sweetness of lactose is 16, the sweetness of galactose is 32 and the sweetness of glucose is 74.3, a calculation of the relative sweetness of the final fermented product generates a sweetness about 3.5 times sweeter when fermented with CHCC16404 than with the strain CHCC14994.

in a standard setup for yoghurt production, 9.5% B-milk was inoculated with 0.1% of a *Lactobacillus delbrueckii* subsp. *bulgaricus* culture grown over night anaerobically in MRS-IM broth containing 2% lactose and 0.9% of a *Streptococcus thermophilus* culture grown over night in M17 broth containing 2% galactose (CHCC15757) or 2% sucrose (CHCC16404). The acidification was followed with an INTAB PC logger and Easyview software. After 30 hours of acidification, milk samples were taken for HPLC analysis to measure the amount of different sugars and acids. The HPLC data are presented in Table 4.

It can be taken from Table 4 that the use of the 2-deoxyglucose-resistant mutant strain CHCC15757 and CHCC16404 of *Streptococcus thermophilus* results in secretion of glucose into the milk irrespective of whether it is combined with a *Lactobacillus delbrueckii* subsp. *bulgaricus* mother strain or with a 2-deoxyglucose-resistant mutant thereof. However, glucose concentrations are higher when a combination of 2-deoxyglucose-resistant mutant strains of both species are used, e.g. a combination of CHCC15757 and CHCC16159, or a combination of CHCC15757 and CHCC16150. When using these mixed cultures, at least 82% of the lactose was found to be consumed, and between 11.8 mg/ml and 14.1 mg/ml of glucose was found to be excreted. Similar results are obtained when the *Streptococcus ther-*

TABLE 3

HPLC data of milk samples.

| Sample No. | Amount mg/ml Citric acid | Amount mg/ml Lactic acid | Amount mg/ml Acetic acid | Amount mg/ml Galactose | Amount mg/ml Glucose | Amount mg/ml Lactose | Sweetness |
|---|---|---|---|---|---|---|---|
| Detection limit | <1.25 | <1.25 | <1.25 | <1.5 | <1.5 | <1.5 | |
| Milk | 1.8 | 1.7 | <1.25 | <1.5 | <1.5 | 47.6 | 762 |
| CHCC16404 + 0.01% sucrose | 1.9 | 5.4 | <1.25 | 16.1 | 23.9 | <1.5 | 2291 |
| CHCC16404 + 0.02% sucrose | 2.0 | 5.6 | <1.25 | 17.0 | 25.3 | <1.5 | 2424 |
| CHCC16404 + 0.03% sucrose | 2.0 | 5.6 | <1.25 | 16.4 | 24.1 | <1.5 | 2315 |
| CHCC16404 + 0.05% sucrose | 2.1 | 6.0 | <1.25 | 17.3 | 25.4 | <1.5 | 2441 |

Sweetness caculated: mg/ml glucose *74 + mg/ml lactose *16 + mg/ml galactose * 32.

Example 11

Carbohydrate Analysis of Milk Fermented with a Combination of Strains of *Streptococcus thermophilus* and Strains of *Lactobacillus delbrueckii* subsp. *bulgaricus*

In this experiment, the concentrations of sugars and organic acids were determined in milk fermented with combinations of a *Lactobacillus delbrueckii* subsp. *bulgaricus* strain (selected from CHCC759, CHCC10019, CHCC16159 and CHCC16160) and a *Streptococcus thermophilus* strain which was either CHCC14994, CHCC15757 or CHCC16404.

The production of yoghurt normally involves the use of a mixed starter culture containing both *Lactobacillus delbrueckii* subsp. *bulgaricus* and *Streptococcus thermophilus* strains. Typically, the milk substrate used in the production of yoghurt is inoculated with 1 part *Lactobacillus delbrueckii* subsp. *bulgaricus* and 9 parts *Streptococcus thermophilus*. In order to analyse glucose secretion capabilities

*mophilus* strain is CHCC15887 which is also a 2-deoxyglucose resistant mutant with a mutation in the glcK gene.

At the same time, the presence of a 2-deoxyglucose-resistant mutant strain in the starter culture also resulted in excretion of more galactose. When a combination of mutant strains, e.g. CHCC15757 and CHCC16159 is used, galactose excretion is about 3 times higher (17.1 mg/ml) compared to a starter culture comprising the corresponding mother strains CHCC14994 and CHCC10019.

Glucose secretion is even more efficient when a combination of the hyper-lactose fermenting and glucose secreting *Streptococcus thermophilus* mutant CHCC16404 and the 2-deoxyglucose-resistant mutant strains of *Lactobacillus delbrueckii* subsp. *bulgaricus* are used, e.g. a combination of CHCC16404 and CHCC16159, or a combination of CHCC16404 and CHCC16160.

Taking into account that the sweetness of sucrose is a 100 (reference value), and the sweetness of lactose is 16, the sweetness of galactose is 32 and the sweetness of glucose is 74, a calculation of the relative sweetness of the final fermented product, presented in last row of Table 4, suggests that the different combination of strains enables the definition of the final concentration of residual lactose, glucose and galactose in the final fermented product. If a yoghurt with maximum inner sweetness due to high concentrations of secreted glucose and galactose and no residual lactose is desired then the most efficient combination of strains is CHCC16404 and CHCC16160. This combination provided a yoghurt that is 3.6 times more sweet that the corresponding combination of 2-DG sensitive strains of *Streptococcus thermophilus* and *Lactobacillus delbrueckii* subsp. *bulgaricus*, CHCC14994 and CHCC10019 and has no detectable lactose left in the fermented milk.

CHCC16159 was grown overnight anaerobic at 40° C. in MRS with 2% lactose

Six bottles with 200 ml B-milk are inoculated at 40° C. overnight with a total of 1% of the outgrown cultures having similar optical densities:
1. 1% CHCC 5445 (BB-12®).
2. 0.5% CHCC 5445 (BB-12®)+0.5% CHCC14994
3. 0.5% CHCC 5445 (BB-12®)+0.5% CHCC15757
4. 1% CHCC5445 (BB-12®).
5. 0.5% CHCC 5445 (BB-12®)+0.5% CHCC10019
6. 0.5% CHCC 5445 (BB-12®)+0.5% CHCC16159

TABLE 4

HPLC data of milk samples fermented with mixed cultures

| Strains | Amount mg/ml Citric acid | Amount mg/ml Lactic acid | Amount mg/ml Acetic acid | Amount mg/ml Galactose | Amount mg/ml Glucose | Amount mg/ml Lactose | Sweetness |
|---|---|---|---|---|---|---|---|
| Detection limit | <1.25 | <1.25 | <1.25 | <1.5 | <1.5 | <1.5 | |
| Milk | 1.7 | <1.25 | <1.25 | <1.5 | <1.5 | 51.6 | |
| CHCC14994 + CHCC10019 | 1.8 | 7.6 | <1.25 | 5.7 | <1.5 | 33.6 | 722 |
| CHCC14994 + CHCC16159 | 1.9 | 7.7 | <1.25 | 5.6 | <1.5 | 36.4 | 762 |
| CHCC15757 + CHCC10019 | 1.7 | 9.7 | <1.25 | 12.9 | 6.5 | 13.2 | 1108 |
| CHCC15757 + CHCC16159 | 2.0 | 10.4 | <1.25 | 17.1 | 14.1 | 9.5 | 1743 |
| CHCC14994 + CHCC759 | 1.7 | 7.4 | <1.25 | 5.6 | <1.5 | 31.6 | 686 |
| CHCC14994 + CHCC16160 | 1.8 | 7.3 | <1.25 | 5.5 | <1.5 | 32.4 | 693 |
| CHCC15757 + CHCC759 | 2.1 | 13.8 | <1.25 | 16.6 | 6.5 | 12.2 | 1209 |
| CHCC15757 + CHCC16160 | 2.0 | 8.7 | <1.25 | 13.2 | 11.8 | 8.5 | 1432 |
| CHCC16404 + CHCC10019 | 2.2 | 8.1 | <1.25 | 11.5 | 1.8 | 24.9 | 900.1 |
| CHCC16404 + CHCC16159 | 2.2 | 7.8 | 1.3 | 20.9 | 14.9 | 3.9 | 1838.3 |
| CHCC16404 + CHCC16160 | 2.3 | 7.7 | <1.25 | 23.1 | 22.3 | <1.5 | 2396.1 |
| CHCC16404* + CHCC10019 | 2.1 | 10.7 | <1.25 | 17.7 | 11.9 | 3.2 | 1501.8 |
| CHCC16404* + CHCC16159 | 2.0 | 11.0 | <1.25 | 22.2 | 20.2 | <1.5 | 2211.3 |
| CHCC16404* + CHCC16160 | 2.1 | 6.6 | <1.25 | 18.3 | 25.8 | <1.5 | 2502.5 |

*addition of 0.05% sucrose
Sweetness calculated: mg/ml glucose *74 + mg/ml lactose *16 + mg/ml galactose * 32.

Example 12

Improving the Growth of Bifidobacteria by use of Glucose Secreting Mutants of *Streptococcus thermophilus* and *Lactobacillus delbrueckii* subsp. *bulgaricus*

Some of the most acknowledged probiotic bacteria like *Bifidobacterium, animalis* subsp. *lactis* BB-12® (commercially available from Chr. Hansen A/S, Hoersholm, Denmark) do not grow well when present alone in lactose based medium like milk. In this experiment, we have therefore investigated the effect of combining *Bifidobacterium animalis* subsp. *lactis* BB-12® with a glucose secreting strain of *Streptococcus thermophilus* or *Lactobacillus delbrueckii* subsp. *bulgaricus*.

Experiment 1:
CHCC 5445 (BB-12®) was grown up at anaerobic conditions overnight at 40° C. in MRS+0.05% cysteine chloride.

CHCC14994 was grown overnight at 40° C. in M17 with 2% galactose.

CHCC 15757 was grown overnight at 40° C. in M17 with 2% galactose.

Experiment 2:
CHCC 5445 (BB-12®) was grown up at anaerobic conditions overnight at 40° C. in MRS+0.05% cysteine chloride.

CHCC10019 was grown overnight anaerobic at 40° C. in MRS with 2% lactose

Only bottles 2-3 and 5-6 acidified due to the poor performance of BB-12 in milk. After fermentation, 100 µl of each culture was plated out in different dilutions ($10^{-5}$, $10^{-6}$, $10^{-7}$, $10^{-8}$) on agar plates selecting for growth of BB-12® specifically i.e. MRS+0.05% cystein chloride+tetracycline added 10 ug/ml of tetracycline and then incubated anaerobic overnight at 40° C. The number of colonies was subsequently determined by counting and an average of the results is given in Table 5 as CFU/ml (colony forming units per milliliter).

TABLE 5

CFU/ml of BB-12 in fermented milk cultures

| Experiment | Cultures | Cfu/ml |
|---|---|---|
| 1 | 1% CHCC 5445 (BB-12) | 4.50E+07 |
| 1 | 0.5% CHCC 5445 (BB-12) + 0.5% CHCC14994 | 4.00E+07 |
| 1 | 0.5% CHCC 5445 (BB-12) + 0.5% CHCC15757 | 4.00E+08 |
| 2 | 1% CHCC 5445 (BB-12) | 6.00E+07 |
| 2 | 0.5% CHCC 5445 (BB-12) + 0.5% CHCC10019 | 2.00E+07 |
| 2 | 0.5% CHCC 5445 (BB-12) + 0.5% CHCC16159 | 1.40E+08 |

Only when the glucose secreting mutants of *Streptococcus thermophilus*, CHCC15757 and *Lactobacillus delbrueckii* subsp. *bulgaricus*, CHCC16159 is present together with BB-12®, the growth of BB-12® is boosted and the total cell count presented as CFU/ml is approximately 10×(1 log) higher in these cultures. This result suggests that glucose secreting strains can be used to boost the content of probiotic strains like BB-12® when mixed together in cultures.

Example 13

Genome comparison of CHCC15757 and CHCC16404 and identification of a mutation in the manM gene encoding the IIC$^{Man}$ protein of the glucose/mannose phosphotransferase system (PTS Genomic DNA preparations of CHCC15757 and CHCC16404 were sequenced at Beijing Genomics Institute (BGI, Beijing, China) and assembled and finished using CLC genomic workbench software (CLCBio, Århus, Denmark). The genome sequences of CHCC15757 and CHCC16404 were aligned using the annotated genome sequence of CHRZ1066 as a reference using Mauve 2.3.1 software. After alignment, a single-nucleotide polymorphism (SNP) analysis was performed using the free Mauve 2.3.1 software on both CHCC15757 and CHCC16404. This allowed the identification of a G to T mutation in the GAA codon (glutamic acid) at amino acid position 209 in the manM gene encoding the IIC$^{Man}$ protein of the glucose/mannose PTS. This change introduced a TAA stop codon at position 209 of the protein (FIG. 3) resulting in the production of a truncated, and therefore, nonfunctional IIC$^{Man}$ protein. Therefore, it is contemplated that this mutation results in prevention of the transport of glucose into the cell via the glucose/mannose PTS.

Deposits and Expert Solutions

The applicant requests that a sample of the deposited micro-organisms stated below may only be made available to an expert, until the date on which the patent is granted.

The strain *Streptococcus thermophilus* CHCC15757 has been deposited at Deutsche Sammlung von Mikroorganismen und Zellkulturen (DSMZ) GmbH, Inhoffenstr. 7B, D-38124 Braunschweig, Germany, on 3 Apr. 2012 under the accession No. DSM 25850

The strain *Streptococcus thermophilus* CHCC15887 has been deposited at Deutsche Sammlung von Mikroorganismen und Zellkulturen (DSMZ) GmbH, Inhoffenstr. 7B, D-38124 Braunschweig, Germany, on 3 Apr. 2012 under the accession No. DSM 25851

The strain *Streptococcus thermophilus* CHCC16404 has been deposited at Deutsche Sammlung von Mikroorganismen und Zellkulturen (DSMZ) GmbH, Inhoffenstr. 7B, D-38124 Braunschweig, Germany, on 12 Dec. 2012 under the accession No. DSM 26722.

The strain *Streptococcus thermophilus* CHCC14994 has been deposited at Deutsche Sammlung von Mikroorganismen und Zellkulturen (DSMZ) GmbH, Inhoffenstr. 7B, D-38124 Braunschweig, Germany, on 3 Apr. 2012 under the accession No. DSM 25838.

The strain *Streptococcus thermophilus* CHCC11976 has been deposited at Deutsche Sammlung von Mikroorganismen und Zellkulturen (DSMZ) GmbH, Inhoffenstr. 7B, D-38124 Braunschweig, Germany, on 8 Sep. 2009 under the accession No. DSM 22934.

The strain *Lactobacillus delbrueckii* subsp. *bulgaricus* CHCC759 has been deposited at Deutsche Sammlung von Mikroorganismen und Zellkulturen (DSMZ) GmbH, Inhoffenstr. 7B, D-38124 Braunschweig, Germany, on 6 Sep. 2012 under the accession No. DSM 26419.

The strain *Lactobacillus delbrueckii* subsp. *bulgaricus* CHCC10019 has been deposited at Deutsche Sammlung von Mikroorganismen und Zellkulturen (DSMZ) GmbH, Inhoffenstr. 7B, D-38124 Braurschweig, Germany, on 3 Apr. 2007 under the accession No. DSM 19252.

The strain *Lactobacillus delbrueckii* subsp. *bulgaricus* CHCC16159 has been deposited at Deutsche Sammlung von Mikroorganismen und Zellkulturen (DSMZ) GmbH, Inhoffenstr. 7B, D-38124 Braurschweig, Germany, on 6 Sep. 2012 under the accession No. DSM 26420.

The strain *Lactobacillus delbrueckii* subsp. *bulgaricus* CHCC16160 has been deposited at Deutsche Sammlung von Mikroorganismen und Zellkulturen (DSMZ) GmbH, Inhoffenstr. 7B, D-38124 Braurschweig, Germany, on 6 Sep. 2012 under the accession No. DSM 26421.

The strain *Bifidobacterium animalis* subsp. *lactis* CHCC5445 (BB-12®) has been deposited at Deutsche Sammlung von Mikroorganismen und Zellkulturen (DSMZ) GmbH, Inhoffenstr. 7B, D-38124 Braunschweig, Germany, on 30 Sep. 2003 under the accession No. DSM 15954

The deposits were made according to the Budapest treaty on the international recognition of the deposit of microorganisms for the purposes of patent procedure.

REFERENCES

WO 2011/026863
Pool et al. (2006) Metabolic Engineering 8(5); 456-464
Thompson et al. (1985) J. Bacteriol. 162(1); 217-223
Chervaux et al. (2000). Appl and Environ Microbiol, 66, 5306-5311
Cochu et al. (2003). Appl and Environ Microbiol, 69(9), 5423-5432
Høier et al. (2010) in The Technology of Cheesemaking, 2nd Ed. Blackwell Publishing, Oxford; 166-192.

The invention claimed is:

1. A method for obtaining a non-genetically modified *Streptococcus thermophilus* strain that carries a mutation in the DNA sequence of the glcK gene encoding a glucokinase protein, wherein the mutation inactivates the glucokinase protein or has a negative effect on expression of the gene, comprising:
    (a) selecting and isolating from a pool of *Streptococcus thermophilus* strains derived from a galactose-fermenting *Streptococcus thermophilus* mother strain a pool of *Streptococcus thermophilus* strains which are resistant to 2-deoxyglucose; and
    (b) selecting and isolating from the pool of *Streptococcus thermophilus* strains which are resistant to 2-deoxyglucose a *Streptococcus thermophilus* strain which exhibits a growth rate in M17 medium+2% galactose higher than its growth rate in M17 medium+2% glucose.

2. A method according to claim 1, further comprising:
    (c) selecting and isolating from a pool of 2-deoxyglucose resistant *Streptococcus thermophilus* strains derived from the *Streptococcus thermophilus* strain selected in step (b) a *Streptococcus thermophilus* strain that grows in M17 medium+2% sucrose but that has a growth rate in M17 medium+2% glucose of zero or at least 0-50% reduced compared to the growth rate of the mother strain in M17 medium+2% glucose.

3. The method according to claim 1, wherein the galactose-fermenting mother strain is selected from the group consisting of the *Streptococcus thermophilus* CHCC14994 strain that was deposited at Deutsche Sammlung von Mikroorganismen and Zellkulturen under accession no. DSM 25838, the *Streptococcus thermophilus* CHCC11976 strain that was deposited at Deutsche Sammlung von Mikroorganismen and Zellkulturen under accession no. DSM 22934, and strains derived therefrom.

4. A method according to claim 1, wherein the obtained *Streptococcus thermophilus* strain increases the amount of glucose in 9.5% B-milk to at least 5 mg/ml when inoculated into the 9.5% B-milk at a concentration of $10^6$-$10^7$ CFU/ml and grown at 40° C. for 20 hours.

5. A method according to claim 1, wherein the obtained *Streptococcus thermophilus* strain increases the amount of glucose in 9.5% B-milk with 0.05% sucrose to at least 5 mg/ml when inoculated into the 9.5% B-milk with 0.05% sucrose at a concentration of $10^6$-$10^7$ CFU/ml and grown at 40° C. for 20 hours.

* * * * *

SEQUENCE LISTING

```
<160> NUMBER OF SEQ ID NOS: 6

<210> SEQ ID NO 1
<211> LENGTH: 969
<212> TYPE: DNA
<213> ORGANISM: Streptococcus thermophilus

<400> SEQUENCE: 1
atgagtaaga aactcttagg tattgacctt ggtggaacaa ctgttaagtt tggtattttg      60
actgcagatg gtgaagttca agaaaaatgg gctattgaaa caaatacgtt tgaaaatggt     120
agccacattg ttcctgacat tgtagaatct ttgaaacacc gtttggaatt gtatggactt     180
actgctgaag attttattgg aattggtatg ggatctccag gtgcagttga ccgagaaaat     240
```

```
aaaacagtaa cgggtgcctt taacttgaac tgggcagaaa ctcaagaagt tggctctgtt    300
attgaaaaag aacttggtat tccattcgct attgataatg atgctaatgt ggctgcactg    360
ggtgaacgtt gggttggtgc tggtgctaac aatcggaatg ttgtctttat aacattgggt    420
acaggtgttg gtggcggtgt tatcgctgat ggtaacttaa ttcatggtgt tgccggtgct    480
ggtggggaaa ttggtcacat tattgttgaa cctgacacag gatttgagtg tacttgcgga    540 aacaagggggt gtctggaaac tgtagcttca gcaacaggta ttgtacgtgt agcacatcat    600
ttggcagaaa aatacgaagg aaactcttct attaaagctg ctgtagacaa tggtgagttt    660
gtgacaagta aagatattat cgtagctgct actgaaggta taagtttgc tgacagcatt    720 gttgataaag tctctaaata cctcggactt gcaacagcaa acatctcaaa cattcttaac    780
ccagattctg tcgttatcgg tggtggtgtt tctgccgcag agaattctt gcgtagtcgt    840 gttgaaggat actttacacg ttatgcattc ccacaagttc gccgtacaac aaaagtgaaa    900
ttagcggagc ttggaaatga tgcaggaatc attggagctg ctagtcttgc ttatagtatt    960
gacaaataa                                                           969
```

```
<210> SEQ ID NO 2
<211> LENGTH: 322
<212> TYPE: PRT
<213> ORGANISM: Streptococcus thermophilus

<400> SEQUENCE: 2

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
                20                  25                  30

Glu Thr Asn Thr Phe Glu Asn Gly Ser His Ile Val Pro Asp Ile Val
            35                  40                  45

Glu Ser Leu Lys His Arg Leu Glu Leu Tyr Gly Leu Thr Ala Glu Asp
        50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Ile Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Phe Val Thr Ser Lys
    210                 215                 220

Asp Ile Ile Val Ala Ala Thr Glu Gly Asp Lys Phe Ala Asp Ser Ile
225                 230                 235                 240
```

```
Val Asp Lys Val Ser Lys Tyr Leu Gly Leu Ala Thr Ala Asn Ile Ser
            245                 250                 255

Asn Ile Leu Asn Pro Asp Ser Val Val Ile Gly Gly Val Ser Ala
        260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
        290                 295                 300

Gly Asn Asp Ala Gly Ile Ile Gly Ala Ala Ser Leu Ala Tyr Ser Ile
305                 310                 315                 320

Asp Lys

<210> SEQ ID NO 3
<211> LENGTH: 20
<212> TYPE: DNA
<213> ORGANISM: Streptococcus thermophilus

<400> SEQUENCE: 3
cttgggtaaa aggctctatg                                                   20

<210> SEQ ID NO 4
<211> LENGTH: 25
<212> TYPE: DNA
<213> ORGANISM: Streptococcus thermophilus

<400> SEQUENCE: 4
cgtttttcaa caaaaaagtg ctacc                                             25

<210> SEQ ID NO 5
<211> LENGTH: 828
<212> TYPE: DNA
<213> ORGANISM: Streptococcus thermophilus

<400> SEQUENCE: 5
atgtcagata tgtcaattat ttctgcgatt ttggtcgtag ctgttgcctt ccttgctggt       60
cttgaaagta tccttgacca attccaattc caccaaccac ttgttgcatg taccctcatc      120
ggtgctgcca caggtaacct cactgcaggt atcatgcttg gtggttctct tcaaatgatt      180
acccttgctt gggcaaacat cggtgctgcc gtagctcctg acgttgccct tgcatctgtt      240
gccgctgcca tcattttggt taaaggtggt aaatttacag ctgaaggtat cggtgttgcg      300
attgcaatag ctatcctgct tgcagttgca ggtctcttcc taactatgcc tgttcgtaca      360
gcatctattg cctttgttca tgctgcagat aaagctgcag aacacggaaa catcgctggt      420
gttgaacgtg catactacct cgctctcctt cttcaaggtt tgcgtattgc tgtgccagca      480
gcccttcttc ttgccatccc ggcccaatct gttcaacatg cccttggctt gatgcctgac      540
tggctcaccc atggtttggt tgtcggtggt ggtatggtcg tagccgttgg ttacgccatg      600
attatcaata tgatggctac tcgtgaagtt tggccattct tcgccattgg ttttgctttg      660
gcagcaatta gccaattgac acttatcgct cttagtacca ttggtgttgc catcgccttc      720
atctacctca acctttctaa acaaggtggc ggaaatggtg gcggaaatgg tggcggaact      780
tcatctggtt caggcgaccc aatcggcgat atcttggaag actactag                   828

<210> SEQ ID NO 6
<211> LENGTH: 275
<212> TYPE: PRT
<213> ORGANISM: Streptococcus thermophilus
```

<400> SEQUENCE: 6

```
Met Ser Asp Met Ser Ile Ile Ser Ala Ile Leu Val Val Ala Val Ala
1               5                   10                  15
Phe Leu Ala Gly Leu Glu Ser Ile Leu Asp Gln Phe Gln Phe His Gln
            20                  25                  30
Pro Leu Val Ala Cys Thr Leu Ile Gly Ala Ala Thr Gly Asn Leu Thr
            35                  40                  45
Ala Gly Ile Met Leu Gly Gly Ser Leu Gln Met Ile Thr Leu Ala Trp
50                  55                  60
Ala Asn Ile Gly Ala Ala Val Ala Pro Asp Val Ala Leu Ala Ser Val
65                  70                  75                  80
Ala Ala Ala Ile Ile Leu Val Lys Gly Gly Lys Phe Thr Ala Glu Gly
                85                  90                  95
Ile Gly Val Ala Ile Ala Ile Ala Ile Leu Leu Ala Val Ala Gly Leu
            100                 105                 110
Phe Leu Thr Met Pro Val Arg Thr Ala Ser Ile Ala Phe Val His Ala
            115                 120                 125
Ala Asp Lys Ala Ala Glu His Gly Asn Ile Ala Gly Val Glu Arg Ala
            130                 135                 140
Tyr Tyr Leu Ala Leu Leu Leu Gln Gly Leu Arg Ile Ala Val Pro Ala
145                 150                 155                 160
Ala Leu Leu Leu Ala Ile Pro Ala Gln Ser Val Gln His Ala Leu Gly
                165                 170                 175
Leu Met Pro Asp Trp Leu Thr His Gly Leu Val Val Gly Gly Gly Met
            180                 185                 190
Val Val Ala Val Gly Tyr Ala Met Ile Ile Asn Met Met Ala Thr Arg
            195                 200                 205
Glu Val Trp Pro Phe Phe Ala Ile Gly Phe Ala Leu Ala Ala Ile Ser
            210                 215                 220
Gln Leu Thr Leu Ile Ala Leu Ser Thr Ile Gly Val Ala Ile Ala Phe
225                 230                 235                 240
Ile Tyr Leu Asn Leu Ser Lys Gln Gly Gly Gly Asn Gly Gly Gly Asn
                245                 250                 255
Gly Gly Gly Thr Ser Ser Gly Ser Gly Asp Pro Ile Gly Asp Ile Leu
            260                 265                 270
Glu Asp Tyr
            275
```